US012778481B2

(12) United States Patent
Vajdic et al.

(10) Patent No.: US 12,778,481 B2
(45) Date of Patent: Nov. 3, 2026

(54) AMBULATORY ELECTROCARDIOGRAM PATCH DEVICES AND METHODS

(71) Applicant: HeartBeam, Inc., Santa Clara, CA (US)

(72) Inventors: Branislav Vajdic, Los Gatos, CA (US); Dorin Panescu, San Jose, CA (US); Bosko Bojovic, Belgrade (RS); Ljupco Hadzievski, Belgrade (RS); Vladan Vukcevic, Belgrade (RS); Uros Mitrovic, Belgrade (RS); Marjan Miletic, Belgrade (RS)

(73) Assignee: HeartBeam, Inc., Santa Clara, CA (US)

( * ) Notice: Subject to any disclaimer, the term of this patent is extended or adjusted under 35 U.S.C. 154(b) by 0 days.

(21) Appl. No.: 18/260,318

(22) PCT Filed: Jan. 4, 2022

(86) PCT No.: PCT/US2022/011075
§ 371 (c)(1),
(2) Date: Jul. 3, 2023

(87) PCT Pub. No.: WO2022/147520
PCT Pub. Date: Jul. 7, 2022

(65) Prior Publication Data

US 2024/0215896 A1 Jul. 4, 2024

Related U.S. Application Data

(63) Continuation of application No. 17/202,299, filed on Mar. 15, 2021, now Pat. No. 11,071,490.
(Continued)

(51) Int. Cl.
*A61B 5/332* (2021.01)
*A61B 5/00* (2006.01)
(Continued)

(52) U.S. Cl.
CPC ............ *A61B 5/332* (2021.01); *A61B 5/0006* (2013.01); *A61B 5/282* (2021.01); *A61B 5/316* (2021.01);
(Continued)

(58) Field of Classification Search
CPC ......... A61B 5/332; A61B 5/361; A61B 5/282; A61B 5/341; A61B 5/316; A61B 5/0006;
(Continued)

(56) References Cited

U.S. PATENT DOCUMENTS 4,216,780 A 8/1980 Rubel
4,850,370 A 7/1989 Dower
(Continued)

FOREIGN PATENT DOCUMENTS

CN 1668242 A 9/2005
CN 101524272 A 9/2009
(Continued)

OTHER PUBLICATIONS

Blanco-Velasco et al.; ECG signal denoising and baseline wander correction based on the empirical mode decomposition; Computers in biology and medicine; 38(1); pp. 1-13; Jan. 1, 2008.
(Continued)

*Primary Examiner* — Adam Z Minchella
(74) *Attorney, Agent, or Firm* — Shay Glenn LLP

(57) ABSTRACT

Methods and apparatuses, including devices and systems, for remote and detection and/or diagnosis of acute myocardial infarction (AMI). In particular, described herein are handheld and adhesive devices having an electrode configuration capable of recording three orthogonal ECG lead signals in an orientation-specific manner, and transmitting these signals to a processor. The processor may be remote or local, and it may automatically or semi-automatically detect AMI, atrial fibrillation or other heart disorders based on the
(Continued)

analyses of the deviation of the recorded 3 cardiac signals with respect to previously stored baseline recordings.

17 Claims, 15 Drawing Sheets

Related U.S. Application Data

(60) Provisional application No. 63/133,669, filed on Jan. 4, 2021.

(51) Int. Cl.

| | |
|---|---|
| ***A61B 5/25*** | (2021.01) |
| ***A61B 5/28*** | (2021.01) |
| ***A61B 5/282*** | (2021.01) |
| ***A61B 5/316*** | (2021.01) |
| ***A61B 5/341*** | (2021.01) |
| ***A61B 5/361*** | (2021.01) |
| ***G16H 40/63*** | (2018.01) |
| ***G16H 40/67*** | (2018.01) |
| ***G16H 50/20*** | (2018.01) |
| ***G16Z 99/00*** | (2019.01) |

(52) U.S. Cl.
CPC .............. *A61B 5/341* (2021.01); *A61B 5/361* (2021.01); *A61B 5/6823* (2013.01); *A61B 5/6825* (2013.01); *A61B 5/684* (2013.01); *A61B 5/6898* (2013.01); *A61B 5/747* (2013.01); *G16H 40/63* (2018.01); *G16H 40/67* (2018.01); *G16H 50/20* (2018.01); *G16Z 99/00* (2019.02); *A61B 2560/0468* (2013.01); *A61B 2562/0209* (2013.01)

(58) Field of Classification Search
CPC ..... A61B 5/6823; A61B 5/6825; A61B 5/684; A61B 5/6898; A61B 5/747; A61B 2560/0468; A61B 2562/0209; A61B 5/26; G16H 40/67; G16H 50/20; G16H 40/63; G16Z 99/00
See application file for complete search history.

(56) References Cited

U.S. PATENT DOCUMENTS

| | | | |
|---|---|---|---|
| 5,339,823 | A | 8/1994 | Reinhold, Jr. |
| 5,630,664 | A | 5/1997 | Farrelly |
| 5,724,580 | A | 3/1998 | Levin et al. |
| 6,047,203 | A | 4/2000 | Sackner et al. |
| 6,052,615 | A | 4/2000 | Feild et al. |
| 6,363,274 | B1 | 3/2002 | Scalisi et al. |
| 6,507,753 | B1 | 1/2003 | Xue et al. |
| 6,607,480 | B1 | 8/2003 | Bousseljot et al. |
| 6,625,483 | B2 | 9/2003 | Hoium et al. |
| 6,760,620 | B2 | 7/2004 | Sippens Groenewegen |
| 7,266,408 | B2 | 9/2007 | Bojovic et al. |
| 7,477,935 | B2 | 1/2009 | Palreddy et al. |
| 7,647,093 | B2 | 1/2010 | Bojovic et al. |
| 7,801,591 | B1 | 9/2010 | Shusterman |
| 8,209,002 | B2 | 6/2012 | Vajdic et al. |
| 8,301,232 | B2 | 10/2012 | Albert et al. |
| 8,369,936 | B2 | 2/2013 | Farringdon et al. |
| 8,615,290 | B2 | 12/2013 | Lin et al. |
| 8,676,304 | B2 | 3/2014 | Fischell et al. |
| 8,700,137 | B2 | 4/2014 | Albert |
| 8,781,566 | B2 | 7/2014 | John et al. |
| 8,818,482 | B2 | 8/2014 | Phillips et al. |
| 9,005,129 | B2 | 4/2015 | Venkatraman et al. |
| 9,364,158 | B2 | 6/2016 | Banet et al. |
| 9,980,678 | B2 | 5/2018 | Chan et al. |
| 10,117,592 | B2 | 11/2018 | Bojovic et al. |
| 10,154,460 | B1 | 12/2018 | Miller et al. |
| 10,433,744 | B2 | 10/2019 | Bojovic et al. |
| 10,499,850 | B2 | 12/2019 | Fuerst et al. |
| 10,709,339 | B1 | 7/2020 | Lusted |
| 10,729,347 | B1 | 8/2020 | Schleicher |
| 11,071,490 | B1 | 7/2021 | Vajdic et al. |
| 11,234,658 | B2 | 2/2022 | Persen et al. |
| 11,412,972 | B2 | 8/2022 | Persen et al. |
| 11,419,538 | B2 | 8/2022 | Vajdic et al. |
| 11,445,963 | B1 | 9/2022 | Belicev et al. |
| 11,529,085 | B1 | 12/2022 | Vajdic |
| 11,701,049 | B2 | 7/2023 | Shvilkin et al. |
| 11,717,253 | B2 | 8/2023 | Jones |
| 2002/0045836 | A1 | 4/2002 | Alkawwas |
| 2003/0032871 | A1 | 2/2003 | Selker et al. |
| 2003/0083586 | A1 | 5/2003 | Ferek-Petric |
| 2003/0083587 | A1 | 5/2003 | Ferek-Petric |
| 2004/0015091 | A1 | 1/2004 | Greenwald et al. |
| 2004/0087864 | A1 | 5/2004 | Grouse |
| 2004/0092836 | A1 | 5/2004 | Ritscher et al. |
| 2004/0138574 | A1 | 7/2004 | Groenewegen et al. |
| 2005/0027203 | A1 | 2/2005 | Umeda et al. |
| 2005/0049663 | A1 | 3/2005 | Harris et al. |
| 2005/0215918 | A1 | 9/2005 | Frantz et al. |
| 2005/0234354 | A1 | 10/2005 | Rowlandson et al. |
| 2006/0009698 | A1 | 1/2006 | Banet et al. |
| 2006/0030782 | A1 | 2/2006 | Shennib |
| 2006/0224072 | A1 | 10/2006 | Shennib |
| 2006/0244465 | A1 | 11/2006 | Kroh et al. |
| 2007/0021677 | A1 | 1/2007 | Markel |
| 2007/0100666 | A1 | 5/2007 | Stivoric et al. |
| 2007/0293781 | A1 | 12/2007 | Sims et al. |
| 2008/0027330 | A1 | 1/2008 | Naghavi et al. |
| 2008/0113650 | A1 | 5/2008 | Engstrom |
| 2008/0161715 | A1 | 7/2008 | Stivoric et al. |
| 2008/0281180 | A1 | 11/2008 | Choe |
| 2009/0112105 | A1 | 4/2009 | Clayman |
| 2009/0281421 | A1 | 11/2009 | Culp et al. |
| 2009/0281440 | A1 | 11/2009 | Farazi et al. |
| 2009/0299206 | A1 | 12/2009 | Wang et al. |
| 2010/0017420 | A1 | 1/2010 | Archer et al. |
| 2010/0023081 | A1 | 1/2010 | Audet et al. |
| 2010/0042008 | A1 | 2/2010 | Amitai et al. |
| 2010/0076331 | A1 | 3/2010 | Chan et al. |
| 2010/0130845 | A1 | 5/2010 | Clayman |
| 2010/0168593 | A1 | 7/2010 | Sakoda et al. |
| 2010/0174204 | A1 | 7/2010 | Danteny |
| 2010/0240980 | A1 | 9/2010 | Zhu et al. |
| 2011/0015496 | A1 | 1/2011 | Sherman et al. |
| 2011/0105928 | A1 | 5/2011 | Bojovic et al. |
| 2011/0124979 | A1 | 5/2011 | Heneghan et al. |
| 2011/0152957 | A1 | 6/2011 | Shaquer |
| 2011/0224565 | A1 | 9/2011 | Ong et al. |
| 2011/0237922 | A1* | 9/2011 | Parker, III ............ A61B 5/1112 600/382 |
| 2011/0301435 | A1 | 12/2011 | Albert et al. |
| 2011/0306859 | A1 | 12/2011 | Saldivar et al. |
| 2012/0022385 | A1 | 1/2012 | Shimuta et al. |
| 2012/0059271 | A1 | 3/2012 | Amitai et al. |
| 2012/0089037 | A1 | 4/2012 | Bishay |
| 2012/0116176 | A1 | 5/2012 | Moravec et al. |
| 2012/0116240 | A1 | 5/2012 | Chou |
| 2012/0136266 | A1 | 5/2012 | Grady |
| 2012/0184858 | A1 | 7/2012 | Harlev et al. |
| 2012/0283586 | A1 | 11/2012 | Song et al. |
| 2012/0306652 | A1 | 12/2012 | Musiol et al. |
| 2013/0125906 | A1 | 5/2013 | Hon |
| 2013/0172723 | A1 | 7/2013 | Baxi et al. |
| 2013/0331665 | A1 | 12/2013 | Libbus et al. |
| 2014/0086346 | A1 | 3/2014 | Mottaiyan et al. |
| 2014/0114166 | A1* | 4/2014 | Baxi ........................ A61B 5/28 600/384 |
| 2014/0155723 | A1 | 6/2014 | Levin et al. |
| 2014/0163349 | A1 | 6/2014 | Amitai et al. |
| 2014/0221845 | A1 | 8/2014 | Mestha et al. |
| 2014/0257122 | A1 | 9/2014 | Ong et al. |
| 2014/0322945 | A1 | 10/2014 | Selvitelli et al. |
| 2014/0333332 | A1 | 11/2014 | Matsumoto et al. |
| 2015/0018660 | A1 | 1/2015 | Thomson et al. |
| 2015/0018693 | A1 | 1/2015 | Mestha et al. |

(56) References Cited

U.S. PATENT DOCUMENTS

| | | | |
|---|---|---|---|
| 2015/0057512 A1 | 2/2015 | Kapoor | |
| 2015/0119780 A1 | 4/2015 | DeLuke et al. | |
| 2015/0257644 A1 | 9/2015 | Cao | |
| 2015/0351646 A1 | 12/2015 | Cervini | |
| 2016/0000834 A1 | 1/2016 | Kinsey et al. | |
| 2016/0015286 A1 | 1/2016 | Gitlin et al. | |
| 2016/0022162 A1 | 1/2016 | Ong et al. | |
| 2016/0045166 A1 | 2/2016 | Gheeraert et al. | |
| 2016/0095527 A1 | 4/2016 | Thng et al. | |
| 2016/0106378 A1 | 4/2016 | Kyal et al. | |
| 2016/0113541 A1 | 4/2016 | Hadley et al. | |
| 2016/0135706 A1 | 5/2016 | Sullivan et al. | |
| 2016/0188823 A1 | 6/2016 | Rowlandson et al. | |
| 2016/0287172 A1 | 10/2016 | Morris et al. | |
| 2016/0296132 A1* | 10/2016 | Bojovic | A61B 5/0006 |
| 2016/0302677 A1 | 10/2016 | He | |
| 2016/0361023 A1 | 12/2016 | Martin et al. | |
| 2017/0049340 A1 | 2/2017 | Cho et al. | |
| 2017/0105682 A1 | 4/2017 | MacDonald et al. | |
| 2017/0127966 A1 | 5/2017 | Wu et al. | |
| 2017/0188861 A1 | 7/2017 | Schreck et al. | |
| 2017/0258342 A1 | 9/2017 | Ukil et al. | |
| 2017/0319082 A1 | 11/2017 | Sayme | |
| 2017/0332942 A1 | 11/2017 | Pflugh et al. | |
| 2017/0340218 A1 | 11/2017 | Kuchler et al. | |
| 2018/0004904 A1 | 1/2018 | Phillips | |
| 2018/0043134 A1 | 2/2018 | Alvarez et al. | |
| 2018/0064356 A1 | 3/2018 | Mendenhall et al. | |
| 2018/0116607 A1 | 5/2018 | Yu et al. | |
| 2018/0116626 A1 | 5/2018 | Darbari et al. | |
| 2018/0125385 A1 | 5/2018 | Chauhan et al. | |
| 2018/0199824 A1 | 7/2018 | Centen et al. | |
| 2018/0316781 A1 | 11/2018 | Salem | |
| 2018/0336969 A1 | 11/2018 | Jabourian | |
| 2019/0069789 A1 | 3/2019 | Bojovic et al. | |
| 2019/0117100 A1 | 4/2019 | Rollie et al. | |
| 2019/0192075 A1 | 6/2019 | Kranz | |
| 2019/0290147 A1 | 9/2019 | Persen et al. | |
| 2019/0298200 A1 | 10/2019 | Wiesel | |
| 2019/0298209 A1 | 10/2019 | Persen et al. | |
| 2019/0336020 A1 | 11/2019 | Kranz | |
| 2020/0113454 A1 | 4/2020 | Wu et al. | |
| 2020/0315480 A1* | 10/2020 | Hwang | A61B 5/002 |
| 2020/0375493 A1 | 12/2020 | Kranz | |
| 2021/0113136 A1 | 4/2021 | Bojovic et al. | |
| 2021/0137392 A1* | 5/2021 | Hwang | A61B 5/361 |
| 2021/0153837 A1 | 5/2021 | Jones | |
| 2021/0169392 A1 | 6/2021 | Albert et al. | |
| 2021/0267525 A1 | 9/2021 | Albert | |
| 2022/0015653 A1 | 1/2022 | Persen et al. | |
| 2022/0015680 A1 | 1/2022 | Vajdic et al. | |
| 2022/0039726 A1 | 2/2022 | Vlaskalic et al. | |
| 2022/0061759 A1 | 3/2022 | Galeev et al. | |
| 2022/0211287 A1 | 7/2022 | Vajdic et al. | |
| 2022/0386929 A1 | 12/2022 | Persen et al. | |
| 2023/0086822 A1 | 3/2023 | Stefano | |
| 2023/0106036 A1 | 4/2023 | Belicev et al. | |
| 2024/0023868 A1 | 1/2024 | Vajdic et al. | |
| 2025/0359803 A1 | 11/2025 | Shvilkin et al. | |

FOREIGN PATENT DOCUMENTS

| | | | |
|---|---|---|---|
| CN | 202854760 | U | 4/2013 |
| CN | 203000927 | U | 6/2013 |
| CN | 105147274 | A | 12/2015 |
| CN | 106691423 | A | 5/2017 |
| EP | 1227752 | A1 | 8/2002 |
| EP | 0944353 | B1 | 11/2002 |
| EP | 1659936 | A1 | 3/2005 |
| EP | 4144288 | A1 | 3/2023 |
| JP | H0391304 | U | 9/1991 |
| JP | 2007195690 | A | 8/2007 |
| KR | 20150083000 | A | 7/2015 |
| KR | 102213513 | B1 | 2/2021 |
| WO | WO01/70105 | A2 | 9/2001 |
| WO | WO2015/177594 | A2 | 11/2015 |
| WO | WO2017/208040 | A2 | 12/2017 |
| WO | WO2019/191487 | A1 | 10/2019 |
| WO | WO2020/167154 | A1 | 8/2020 |
| WO | WO2020/232040 | A1 | 11/2020 |
| WO | WO2022/104160 | A1 | 5/2022 |
| WO | WO2022/147520 | A1 | 7/2022 |
| WO | WO2023/060119 | A1 | 4/2023 |

OTHER PUBLICATIONS

Jonkman et al.; Estimated ECG Subtraction method for removing ECG artifacts in esophageal recordings of diaphragm EMG. Biomedical Signal Processing and Control; vol. 69; Article 102861; Aug. 1, 2021.

Marouf et al; Algorithm for EMG noise level approximation in ECG signals; Biomedical Signal Processing and Control; vol. 34; pp. 158-165; Apr. 1, 2017.

Kikillus et al; Three different algorithms for identifying patients suffering from atrial fibrillation during atrial fibrillation free phases of the ECG; Computers in Cardiology; IEEE; pp. 801-804; Sep. 2007.

Meredith et al.; Photoplethysmographic derivation of respiratory rate: a review of relevant physiology; Journal of Medical Engineering and Technology; doi:10.3109/03091902.2011.638965; pp. 60-66; Mar. 2012.

Park et al.; Real-time estimation of respiratory rate from a photoplethysmogram using an adaptive lattice notch filter; Biomedical Engineering Online; 13:170; pp. 1-7; Dec. 2014.

Persen et al.; U.S. Appl. No. 16/035,568 entitled "Systems, methods, and computer software for health monitoring and guidance," 31 pages, filed Jul. 13, 2018.

Pirhonen et al.; Acquiring respiration rate from photoplethysmographic signal by recursive bayesian tracking of intrinsic modes in time-frequency spectra; Sensors; 1896); doi:10.3390/s18061693; 16 pages; May 2018.

Sioni et al.; Stress detection using physiological sensors; Computer; 48(10); pp. 26-33; 12 pages; Oct. 2015.

Atanasoski et al.; U.S. Appl. No. 18/595,410 entitled "Methods and apparatus for electromyography noise elimination from electrocardiogram signals by iterative regeneration," filed Mar. 4, 2024.

Vajdic et al.; U.S. Appl. No. 18/608,813 entitled "Apparatus for generating an electrocardiogram," filed Mar. 18, 2024.

Bartolo et al.; Analysis of diaphragm EMG signals: comparison of gating vs. subtraction for removal of ECG contamination; Journal of applied physiology; 80(6); pp. 1898-1902; Jun. 1, 1996.

Dower et al.; A clinical comparison of three vog lead systems using resistance-combining networks; American Heart Journal; 55(4); pp. 523-534; Apr. 1958.

Goff et al.; 2013 ACC/AHA guideline on the assessment of cardiovascular risk: a report of the American College of Cardiology/American Heart Association Task Force on Practice Guidelines; Journal of the American College of Cardiology; 63(25 Part B); pp. 2936-2959; Jul. 1, 2014.

Goff et al.; 2013 ACC/AHA guideline on the assessment of cardiovascular risk: a report of the American College of Cardiology/American Heart Association Task Force on Practice Guidelines; Journal of the American College of Cardiology;; 129(25 Suppl 2): pp. S49-S73; Jun. 2014.

Kligfield et al.; Recommendations for the standardization and interpretation of the electrocardiogram: Part I: The Electrocardiogram and Its Technology A Scientific Statement From the American Heart Association Electrocardiogramd Arrhythmias Committee, Council on Clinical Cardiology; the American College of Cardiology Foundation: and the Heart Rhythm Society Endorsed by the International Society for Computerized Electrocardiology; 49(10); pp. 1109-1127, Mar. 13, 2007.

Marma et al.; Systematic examination of the updated Framingham heart study general cardiovascular risk profile; Circulation; 120(5): pp. 384; Aug. 1, 2009.

Med-Tech Innovation; The ECG device the of a credit card; Aug. 23, 2017; retrieved from the internet (https://www.med-technews.com/news/the-ecg-device-the-size-of-a-credit-card/) on Jan. 26, 2021.

(56) References Cited

OTHER PUBLICATIONS

Perk et al.; European Guidelines on cardiovascular disease prevention in clinical practice (version 2012) The Fifth Joint Task Force of the European Society of Cardiology and Other Societies on Cardiovascular Disease Prevention in Clinical Practice; European heart Journal; 33(13); pp. 1635-1701; Jul. 1, 2012.
Rakshit et al.; EKF with PSO technique for delineation of P and T wave in electrocardiogram (ECG) signal; In 2015 2nd International Conference on Signal Processing and Integrated Networks (SPIN); IEEE; pp. 696-701; Feb. 19, 2015.
Sun et al.; Characteristic wave detection in ECG signal using morphological transform; BMC cardiovascular disorders; 5(1); pp. 1-7; Dec. 2005.
Vajdic; U.S. Appl. No. 18/068,481 entitled "Apparatus for generating an electrocardiogram," filed Dec. 19, 2022.
Vajdic etal.; U.S. Appl. No. 18/252,803 entitled "Compact mobile three-lead cardiac monitoring device with hybrid electrode," filed May 12, 2023.
Shvilkin et al.; U.S. Appl. No. 18/324,111 entitled "Hand held device for automatic cardiac risk and diagnostic assessment," filed May 25, 2023.
Roscoe; Assessing pilot workload. Why measure heart rate, HRV and respiration?; Biological Psychology; 34(2-3); pp. 259-287; Nov. 1992.
Vajdic et al.; U.S. Appl. No. 18/985,015 entitled "Compact mobile three-lead cardiac monitoring device," filed Dec. 17, 2024.
Vajdic et al.; U.S. Appl. No. 19/412,849 entitled "Electrocardiogram patch devices and methods," filed Dec. 8, 2025.
apple.com; ECG app and irregular heart rhythm notification available today on Apple Watch; Apple Newsroom; retrieved from the internet (https://www.apple.com/newsroom/2018/12/ecg-app-and-irregular-heart-rhythm-notification-available-today-on-apple-watch/); Dec. 6, 2018.

* cited by examiner

FIG. 6A
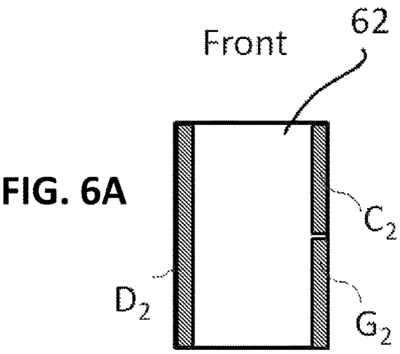
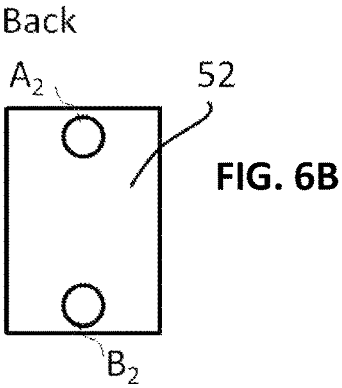
FIG. 6B
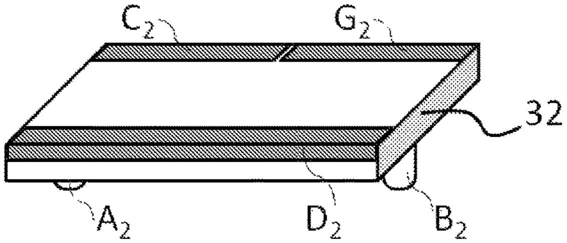
FIG. 6C
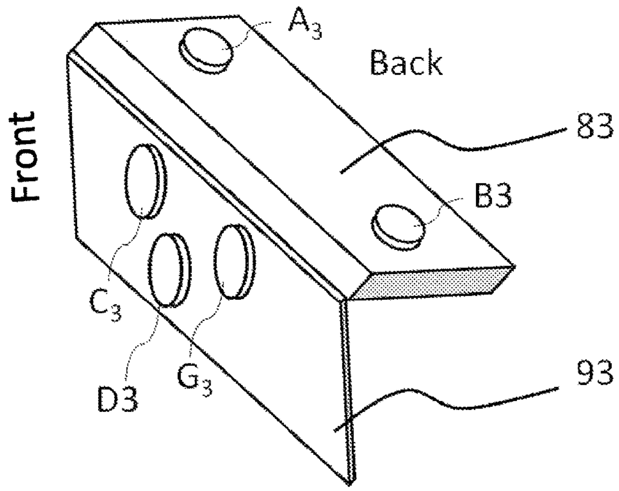
FIG. 7
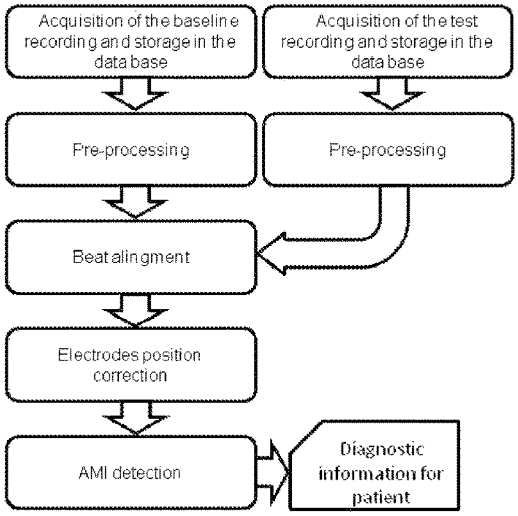
FIG. 8

AMBULATORY ELECTROCARDIOGRAM PATCH DEVICES AND METHODS

PRIORITY CLAIM

This application claims priority to of U.S. patent application Ser. No. 17/202,299, titled "ELECTROCARDIOGRAM PATCH DEVICES AND METHODS," filed Mar. 15, 2021 and to U.S. Provisional Patent Application No. 63/133,669, titled "AMBULATORY ELECTROCARDIOGRAM PATCH DEVICES AND METHODS," filed on Jan. 4, 2021, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses (e.g., systems, devices, etc.) described herein may relate generally to electrocardiography.

BACKGROUND

Acute Myocardial Infarction (AMI, also referred to as heart attack) remains a leading cause of mortality in the developed world. Finding accurate and cost-effective solutions for AMI diagnosis is vital. Survival of patients having AMI may depend critically on reducing treatment delay, and particularly reducing the time between symptoms onset and medical treatment time. A technology that would enable AMI diagnosis early after occurrence of AMI symptoms, for example, at patient's home or wherever the patient may be, may significantly decrease AMI mortality.

In the AMI setting, the conventional 12-lead ECG is not only the most important piece of information, but it is also nearly as important as all other information combined. Therefore, a technology for early AMI diagnosis may rely on ECG recording. The ECG recording may be performed by the patient himself, but such a technology would need to overcome the problem of complicated application of 12-lead ECG electrodes, and to enable automated software-based AMI detection.

Electrocardiogram (ECG) data recording as acquisition of bioelectric signals for cardiac condition status detection is widely known in the art. In general, before the recording is performed, characteristic points on patient's body are identified and electrodes are positioned with respect to these points. During the recording procedure, the electrical voltages between two characteristics points are measured, and corresponding signals are called ECG leads. The conventional ECG uses 10 electrodes to record 12 leads, and the 12 leads ECG (12L ECG) is widely adopted standard in cardiac diagnostics.

It has long been suggested that urgent cardiac diagnostics which enables a patient, wherever he may be, to record his ECG himself and send it to his cardiologist in the remote diagnostic center via commercial telecommunication network (cellular or similar) would be beneficial. On the bases of the received ECG and the conversation with the patient, the cardiologist on duty could decide whether the patient's state requires urgent medical intervention, and act accordingly. There are a number of patents and products which, within the said concept of urgent cardiac diagnostics, offer different solutions for recording and transmitting the ECG signal. The simplest of these devices uses only a single 'lead' or pair of electrodes. However, devices recording only one ECG lead may be used only for rhythm disorders. Because the ECG changes needed for detection of an AMI may occur in as few as only two among 12 leads of a conventional ECG, it may be difficult, to reliably use only a single lead (or in some cases only a few leads) to reliably and thoroughly detect AMI. Further, it is also unreasonable for a patient to record a full 12L ECG by himself, because of the difficulty in placing the leads.

Solutions capable of detecting AMI that use different surrogates of 12L ECG are also known. For example, Heartview P12 by Aerotel (Aerotel Medical Systems, Holon, Israel), Smartheart, by SHL (SHL Telemedicine, Tel Aviv, Israel) and CardioBip (e.g., U.S. Pat. No. 7,647,093). All these solutions have significant drawbacks. For example, all of these solutions typically require complicated measuring procedures (such as with Heartview, Smartheart), and may require attaching electrodes by the means of cables, taking the clothes off from the waist up, using straps and multi-step recording procedure (e.g., see US20120059271A1 to Amitai et al.). Existing or proposed systems may also require extensive calibration procedures (e.g., Cardiobip), requiring the patient to be in a medical facility with specially trained personnel prior to using the device by himself. Finally, all of these procedures may require medical personnel for interpretation of recorded ECG.

For example, the Cardiobip device is the simplest for use by the patient and allows simple positioning of the device by pressing it against the chest, with no cables or straps, and recording the ECG. In this example, a diagnostic center may use a PC computer with corresponding software for processing of three special ECG leads and reconstruction of the three leads into a standard 12 lead ECG. The reconstruction is required for interpretation of ECG by the medical personnel. Accuracy of the reconstruction of a 12 standard ECG leads using the recordings of three special leads may be achieved by strictly determined arrangement of integrated electrodes in the mobile device and corresponding leads. A hand-held device may include 5 built in electrodes (see, e.g., EP1659936) three of which may be placed in contact with the chest of the patient and the remaining two electrodes in contact with right- and left-hand fingers. The reconstruction algorithm in the Cardiobip device is premised on the assumption that the diffuse electric activity of the heart muscle can be approximated by a time-changing electrical dipole (heart dipole) immersed in a low conducting environment. The Heart dipole is represented by a vector defined by three non-coplanar projections, so that it can be determined on the basis of recording of electric potential between any three pairs of points corresponding to three non-coplanar directions, i.e., three special ECG leads not lying on the same plane. Standard ECG leads are reconstructed as linear combinations of the recorded special leads and coefficients by which the transformation matrix is defined. It can be shown, by an in-depth analysis, that there are two dominant error sources in such reconstruction. Unfortunately, the heart dipole is only the first term in the multipole mathematical expansion of diffuse heart electrical activity and this approximation is valid only for recording points at a sufficient distance from the heart. In the points near the heart, the linearity of the system necessary for signal reconstruction is significantly affected by the non-dipole content created due to the presence of higher order terms in multipole expansion.

Further the described reconstruction techniques for converting a few leads into a 12-lead signal for analysis by a cardiologist or other technical expert are also limited. In order to carry enough diagnostic information the three special leads need to be as close to orthogonal as possible (e.g., three vector axes with 90 degrees angle between each of them). The opposite to orthogonal is the case of three coplanar vectors, that is three vectors in the same plane, in which case the diagnostic information corresponding to the axis perpendicular to that plane is completely missing. Importantly the assumptions needed for this modeling, treating the heart as a dipole (and estimating at a distance) and making orthogonal measurements of the heart leads, are at odds with each other, since the orthogonal lead positions are far easier to obtain if the electrodes are closer to the heart, while in this case the non-dipole content is higher. Existing systems such as Cardiobip must rely on the use of a configuration that optimally fulfills both requirements, in which all three leads use the right-hand electrode as a reference. These systems also have additional drawbacks. For example, Cardiobip uses three integrated electrodes on the chest side of the device. It was observed in clinical studies using Cardiobip that breast in female patients and pronounced pectoralis muscle in male patients may prevent a reliable contact of all three electrodes with the chest surface simultaneously. It has also been observed that the symmetrical arrangement of finger electrodes on the front side of the device may cause switching of left- and right-hand fingers in about 10% recordings, making the recording useless for diagnostics.

Similarly, other solutions that use a reduced set of three leads (e.g., US20140163349A1; US20100076331) typically use the three leads that are coplanar and therefore lack enough diagnostic information for AMI detection.

In addition, the requirement for trained medical personnel for the interpretation of recorded ECG may be an organizational challenge and increases the operational cost of the system, and the accuracy of the human ECG interpretation may have large variance. Automated software for ECG interpretation is also used in the systems for early diagnosis of AMI, but they have performance that is inferior to that of human interpreters. The chest pain is the main symptom suggesting an AMI, or ischemia (the underlying physiological process). The main ECG parameter used is the ST segment elevation (STE). Unfortunately, a large number of patients (up to 15%) presenting with chest pain have STE of non-ischemic etiology (NISTE) on their presenting (to the emergency room) ECG. Thus, both human readers and automated software may often misinterpret NISTE as a new STE due to ischemia. In a typical emergency room (ER) scenario, patients with chest pain are examined by emergency physician who must promptly decide if the acute ischemia is present, relaying just on the on-site (current) ECG recording.

Thus, it would be advantageous to provide a technology capable of separating new from old STE, as it could significantly increase performance of automated AMI detection, and make it a viable enhancement or even replacement for human interpretation, particularly when qualified human interpretation is not available. Described herein are methods and apparatuses that may address the problems and needs discussed above, particularly the need for early automated remote diagnostics of AMI. In particular the methods and apparatuses described herein may provide a mechanically stable, longer-term and improved electrical contact, while eliminating errors associated with switching of finger contacts. Additionally, aspects of more frequent, or continuous, monitoring are addressed.

SUMMARY OF THE DISCLOSURE

In general, described herein are methods and apparatuses for recording and analyzing cardiac signals to automatically detect one or more indicators of cardiac dysfunction, including in particular AMI. These apparatuses may typically include a housing having at least four electrodes arranged thereon in an asymmetric manner on two or more surfaces to provide orthogonal, or quasi-orthogonal leads.

As used herein, a cardiac signal may refer to a voltage produced by a human heart as sensed between selected points on the surface of a subject's body and may also be referred to as cardiac electrical signals (e.g., electrocardic signals). These cardiac signals may include electrocardiogram (ECG) signals. It should be understood that although the term ECG (electrocardiogram) is commonly used to refer to conventional 12-lead ECG signals, the cardiac signals (cardiac electrical signals) described herein are not limited to these conventional 12-lead ECG signals. Further, although the disclosure herein may use and refer to terms including characteristic points (such as P, Q, R, S, T) and intervals (such as ST segment) on the cardiac signals described, these characteristic points may refer to points, positions or regions equivalent to the positions on conventional 12-lead ECG signals.

Described herein are mobile, hand-held apparatuses for automated cardiac electrical signal analysis. For example, an apparatus may include: a housing having a back, a first side, and a front; a first electrode and a second electrode integrated on the back of the housing configured to measure bioelectric signals from a patient's chest, wherein the first and second electrode are positioned a distance of at least 5 cm apart; a third electrode configured to measure bioelectric signals from the patient's right hand; a fourth electrode configured to measure bioelectric signals from the patient's left hand; wherein one or both of the third electrode and the fourth electrode are integrated on the front of the housing; and a processor within the housing configured to record three orthogonal cardiac leads from the first, second, third and fourth electrodes, wherein less than three pairs of said electrodes comprise the third electrode.

Alternatively or additionally, any of these apparatuses may include: a housing having a back, a first side, and a front; a first electrode and a second electrode integrated on the back of the housing configured to measure bioelectric signals from a patient's chest, wherein the first and second electrode are positioned a distance of at least 5 cm apart; a third electrode configured to measure bioelectric signals from the patient's right hand; a fourth electrode configured to measure bioelectric signals from the patient's left hand; and a processor configured to record 3 orthogonal cardiac leads from the first, second, third and fourth electrodes, wherein the processor comprises a register configure to store a first set of three orthogonal cardiac leads taken at a first time, and a comparator configured to determine a difference signal between the first set of three orthogonal cardiac leads and a second set of three orthogonal cardiac leads taken at a second time.

For example, described herein are mobile, hand-held, three-lead apparatuses for automated electrical cardiac-signal analysis. An apparatus may include: a housing having a back, a first side, and a front, wherein the front is parallel with the back; a first electrode and a second electrode integrated on the back of the housing configured to measure bioelectric signals from a patient's chest, wherein the first and second electrode are positioned a distance of at least 5 cm apart; a third electrode configured to measure bioelectric signals from the patient's right hand; a fourth electrode configured to measure bioelectric signals from the patient's left hand; wherein one or both of the third electrode and the fourth electrode are integrated on the front of the housing; a processing network (e.g. resistive network, op-amp summation network, etc.) connecting at least two of the first, second, third and fourth electrodes, wherein the processing network forms a central point (CP); a processor within the housing configured to record 3 orthogonal, or quasi-orthogonal cardiac leads from the first, second, third and fourth electrodes, wherein less than three pairs of said electrodes comprise the third electrode; and a communication circuit within the housing configured to transmit the 3 cardiac leads to an internal or remote processor.

At least one lead may be formed between one of the said electrodes and the central point (CP) formed by mutually connecting at least two electrodes by the resistive network. For example, the third and fourth (right and left hand) electrodes may be separated by a processing network to form a central point so that at least one lead including the third and fourth electrodes may be measured between the central point and the third or fourth electrode.

In general, the apparatus may be oriented, e.g., including an up and down, relative to the patient's body. The apparatus may include a marker (e.g., one or more of: alphanumeric marker, e.g., label, body shape, light, e.g., LED, etc.). For example, the apparatus may include a marker on the housing indicating the orientation of the housing, such as an LED marker on the housing indicating the orientation of the housing.

The third and fourth electrodes may be disposed on two opposed sides with respect to a longitudinal plane of symmetry of the device housing, said plane of symmetry being substantially perpendicular to the back surface of the device housing.

In any of these variations, a ground electrode may be present on the housing for contacting one of the patient's hands disposed on either the side or front of the housing.

Either the third or fourth electrodes may be band-shaped and disposed along the side of the device housing.

The housing may comprise a mobile phone housing, whereby the third or fourth electrodes are configured as conductive transparent areas on the touch screen of the mobile phone. The housing may be incorporated in a mobile phone housing. The housing may be an extension structure of a mobile phone housing communicating with the said phone using an electrical connector or wireless communication. The housing may forma mobile phone protective case. For example, the housing may forma mobile phone protective case with a phone display protective cover and the third and fourth electrodes incorporated in the phone display protective cover.

In some variations, the apparatus is integrated with or connected to a cover (e.g., back cover) of a mobile phone. For example the housing for the apparatus may be a back cover for a mobile phone that can be retrofitted (e.g., used to replace) a standard back cover of a smartphone or other mobile phone. In some variations, the apparatus can be connected to the cover (e.g., back cover) of the mobile phone, e.g., by an adhesive or other attachment mechanism.

Also described herein are methods of detecting cardiac anomalies, such as detecting ischemia, atrial fibrillation or other cardiac disorder; these methods may be automated methods. Any of these methods may be methods for automated cardiac diagnostics, and may include: acquiring a first set of at least three orthogonal leads from a patient's chest and hands at a first time; acquiring a second set of at least three orthogonal leads from the patient's chest and hands a second time; performing a beat alignment in a processor on the first and second sets of at least three orthogonal leads to synchronize representative beats from the first and second sets of at least three orthogonal leads; calculating a difference signal representing the change between the first and second at least three orthogonal leads; detecting cardiac changes suggestive of a cardiac condition by comparing parameters of the first and second at least three orthogonal leads or by comparing parameters of the difference signal to a predefined threshold; and communicating cardiac changes from the device to the patient.

Alternatively or additionally, a method for automated cardiac diagnostics may include: positioning a device configured to detect at least three orthogonal leads from a patient's chest and hands against the subject's chest in a first recording position; acquiring a first set of at least three orthogonal leads from the device at a first time; communicating the first set of at least three orthogonal leads to a processor; positioning the device against the subject's chest in a second recording position; acquiring a second set of at least three orthogonal leads from the patient using the device at a second time; communicating the second set of at least three orthogonal leads to the processor; performing a beat alignment in the processor to synchronize representative beats from the first and second sets of at least three orthogonal leads; calculating a difference signal representing the change between the first and second sets of at least three orthogonal leads; detecting cardiac changes suggestive of a cardiac condition by comparing one or more parameters of the difference signal to a predefined threshold; and communicating cardiac changes from the device to the patient.

For example, a method for automated cardiac diagnostics may include: placing a device comprising a housing having four integrated electrodes arranged to measure three orthogonal leads from a patient's chest and hands against the subject's chest in a first recording position; acquiring a first 3 lead cardiac recording (also referred to as three cardiac lead recording and three lead electrical cardiac readings) from the device at a first time (e.g., taking a baseline recordings); communicating the first 3 lead recording to a processor; keeping the device at the same first recording position or placing the device against the subject's chest in a second recording position; acquiring a second 3 lead recording from the device at a second time (diagnostic recordings); communicating the second 3 lead recording to the processor; performing a beat alignment in the processor to synchronize representative beats from the first and second 3 lead recordings; calculating a difference signal representing the change between the first and second 3 cardiac leads recordings; detecting changes in the cardiac signals (e.g., changes in the cardiac signal records, also referred to herein as cardiac changes) suggestive of cardiac conditions, such as ischemia or atrial fibrillation, by comparing parameters of the first and second 3 lead cardiac recording or by comparing parameters of the difference signal to a predefined threshold; and communicating any cardiac changes suggestive of a cardiac condition from the device to the patient.

The first and second recording positions may be different or the same. In some variations, the method (or an apparatus performing the method) may detect if the positions have changed and either correct for the different recording positions or indicate that the hand-held device needs to be more accurately repositioned. For example, the method may include compensating for chest electrode miss-positioning between the first and second recording positions in the processor by compensating a heart electrical axis deviation in a 3 cardiac leads vector space.

Communicating the first 3 lead electrical cardiac recording to the processor may comprise wirelessly transmitting the first 3 lead electrical cardiac recordings to a remote processor, transmitting a partial cardiac-recording processing result to a remote processing, or just transferring the 3-lead cardiac recordings to an internal processor for processing, or for patient alert.

In general, these methods may include pre-processing the first and second 3 lead electrical cardiac recordings in the processor to achieve one or more of: eliminate power line interference, baseline wandering and/or muscle noise; obtain a representative beat using fiducial points and median beat procedure; and check for switching of the left and right finger.

The parameters of the diagnostic recording, baseline recording, and difference signal may be vector magnitude of the cardiac signal, where the vector components are three cardiac leads of the diagnostic, baseline and difference signals in a single time instant (J point, J+80 ms) or average in predetermined time interval (e.g., the ST segment or other predetermined interval) and radius of the sphere which envelopes the vector signal hodograph of the ST segment (or other predetermined interval).

The parameters of the diagnostic recording, baseline recording, and difference signal may be RR variability (or equivalent), amplitude of P waves (or equivalent), or averaged amplitude of P waves when detection of atrial fibrillation or atrial flutter are desired.

Any of these methods may also include transmitting any cardiac signal changes suggestive of a cardiac condition from the processor to the device. The methods may also include communicating any cardiac signal changes suggestive of a cardiac condition from the device to the patient comprises presenting a visual and/or audible alert to the patient.

For example, a method for automated cardiac diagnostics may include: placing a device comprising a housing having four integrated electrodes arranged to measure three orthogonal, or quasi-orthogonal, leads from a patient's chest and hands against the subject's chest in a first recording position; acquiring a first 3 lead cardiac recording from the device at a first time; communicating the first 3 lead cardiac recording to a processor; storing the first 3 lead cardiac recording as baseline recording; keeping the device at the same first location, or placing the device against the subject's chest in a second recording position; acquiring a second 3 lead cardiac recording from the device at a second time; communicating the second 3 lead cardiac recording to the processor; pre-processing the first and second 3 lead cardiac recordings in the processor to eliminate power line interference, baseline wandering and muscle noise, obtain a representative beat using fiducial points and median beat procedure, and to check for switching of the left and right finger; performing beat alignment in the processor to bring representative beats from the first and second 3 lead cardiac recordings in a same time frame so that corresponding points are synchronized; compensating for chest electrode miss-positioning between the first and second recording positions in the processor by compensating a heart electrical axis deviation in a 3 cardiac leads vector space; calculating a difference signal representing the change between the first and second 3 cardiac leads recordings; detecting cardiac signal changes suggestive of cardiac condition (e.g., ischemia, atrial fibrillation, atrial flutter, etc.) by comparing parameters of the first and second 3 lead cardiac recording or by comparing parameters of the difference signal to a predefined threshold; communicating any cardiac signal changes suggestive of a cardiac condition from the device to the patient.

In general, described herein are apparatuses configured to perform any of the methods described herein. For example, an apparatus configured to provide an automated cardiac diagnostics may include: a housing comprising at least four electrodes connected to a processor within the housing; wherein the processor is configured to: acquire a first set of at least three orthogonal leads from a patient's chest and hands at a first time; acquire a second set of at least three orthogonal leads from the patient's chest and hands a second time; perform a beat alignment on the first and second sets of at least three orthogonal leads to synchronize representative beats from the first and second sets of at least three orthogonal leads; calculate a difference signal representing the change between the first and second at least three orthogonal leads; detect cardiac changes suggestive of a cardiac condition by comparing parameters of the first and second at least three orthogonal leads or by comparing parameters of the difference signal to a predefined threshold; and communicate cardiac changes from the device to the patient.

Although the description of the methods and apparatuses included herein describes the use of a set of orthogonal, or quasi-orthogonal, cardiac signals, these methods and apparatuses may be used with any set of signals (cardiac electrical signals) which contain significant independent cardiac information. For example, an implementation that used cardiac leads represented by vectors that are not completely orthogonal would not deviate from the spirit of this invention. It would be important to have the respective cardiac vectors orientated at relative angles greater than 300 with respect to one another. Such smaller relative angles may still provide significantly linearly independent information and allow the apparatuses and methods described herein to produce similar and clinically/diagnostically relevant results. Accordingly, for simplicity, without implying any limitation, we may herein refer to our cardiac leads as orthogonal leads. Thus, orthogonal leads may be strictly orthogonal (e.g., having deviation of the leads relative angles from 900 less than 10°, less than 8°, less than 70, less than 6°, less than 5°, less than 4°, less than 3°, less than 2°, less than 10, etc.) or approximately orthogonal (e.g., having deviation of the leads relative angles from 900 less than 30°, 25°, 20°, 15°, etc.). Alternatively, the quasi-orthogonality can be assessed based on the cross-correlation function of combinations of data from any two leads, data which were required at about the same time and with the same device. Given that herein orthogonality refers to the amount of independent information content, two leads from the set may be deemed quasi-orthogonal if there cross-correlation is less than 0.6.

For example, described herein are adhesive patch devices for synthesizing a 12-lead electrocardiogram. These devices may include: a patch of adhesive material having a back and a front, wherein the back is configured to be adhesively secured to a patient's chest; a first electrode and a second electrode integrated on the back of the patch configured to measure bioelectric signals from the patient's chest, wherein the first and second electrodes are positioned a distance of at least 5 cm apart; a third electrode on the front of the patch and configured to measure bioelectric signals from the patient's right hand; a fourth electrode on the front of the patch and configured to measure bioelectric signals from the patient's left hand; a processing network forming a central point in a sagittal plane through the patient's chest passing between the third and fourth electrodes when the housing is held adhesively secured against the patient's chest, wherein three orthogonal cardiac leads are formed from said electrodes and the central point; and a processor within a housing on the patch configured to process the three orthogonal cardiac leads derived from the first, second, third and fourth electrodes.

For example, an adhesive patch device for synthesizing a 12-lead electrocardiogram, may include: a patch of adhesive material having a back and a front, wherein the back is configured to be adhesively secured to a patient's chest; a first electrode and a second electrode integrated on the back of the patch configured to measure bioelectric signals from the patient's chest, wherein the first and second electrodes are positioned a distance of at least 5 cm apart; a third electrode on the front of the patch and configured to measure bioelectric signals from the patient's right hand; a fourth electrode on the front of the patch and configured to measure bioelectric signals from the patient's left hand; a processing network forming a central point in a sagittal plane through the patient's chest passing between the third and fourth electrodes when the housing is held adhesively secured against the patient's chest, wherein three orthogonal cardiac leads are formed from said electrodes and the central point; and a processor configured to process the three orthogonal cardiac leads, wherein the processor comprises a register configured to store a first set of values for the three orthogonal cardiac leads taken at a first time, and a comparator configured to determine a difference signal between the first set of values of three orthogonal cardiac leads and a second set of values of the three orthogonal cardiac leads taken at a second time.

Any of these devices may include a communication circuit within the housing configured to transmit the processed three orthogonal cardiac leads to a remote processor. The processor may be configured to receive information back from the remote processor. The device may include a marker on the housing indicating the orientation of the patch when applied to the patient's chest. For example, the device may include an LED on the housing indicating the orientation of the housing.

The third and fourth electrodes may be disposed on two opposed sides with respect to a longitudinal plane of symmetry of the housing, said plane of symmetry being substantially perpendicular to the back of the housing. For example, the housing may extend proud of the front of the patch and may include sides (e.g., four sides). In some examples, the device includes a ground electrode (e.g., on the housing) for contacting one of the patient's hands, for example, disposed on either a side or a front of the housing. Either the third or fourth electrode may be band-shaped and disposed along a first side of the housing.

Any of these devices may be configured to operate (and to switch between) different modes of operation, including a 12-lead ECG detection mode, when a detection circuit (e.g., a finger detection circuit) detects both finger electrodes (e.g., the third and fourth electrodes) are in contact with a finger, such as a finger from the patient's left hand and a finger from the patient's right hand. The device may switch to a standby mode (or 1-lead ECG mode) when the detection circuit indicates that neither finger electrode is in contact with a finger. In the standby/1-lead ECG mode the device may be configured to take a 1-lead ECG measurement from just the chest electrodes (the first and second electrodes); these measurements may be taken on a predetermined schedule (e.g., once per day, twice per day, every other day, etc.), and stored, processed and/or transmitted. For example, the processor may be configured to automatically detect a one-lead ECG signal from the first electrode and the second electrode when the detection circuit does not detect the finger contact on both the third electrode and the fourth electrode.

Thus, in general, any of these devices may include a detection circuit configured to detect a finger contact on either or both the third electrode and the fourth electrode. In general, the processor may be configured to collect the three orthogonal leads when the detection circuit detects the finger contact on both the third electrode and the fourth electrode (e.g., in the first mode).

An example of an adhesive patch device for synthesizing a 12-lead electrocardiogram may include: a patch of adhesive material having a back and a front, wherein the back is configured to be adhesively secured to a patient's chest; a first electrode and a second electrode integrated on the back of the patch configured to measure bioelectric signals from the patient's chest, wherein the first and second electrodes are positioned a distance of at least 5 cm apart; a third electrode on the front of the patch and configured to measure bioelectric signals from the patient's right hand; a fourth electrode on the front of the patch and configured to measure bioelectric signals from the patient's left hand; a processing network forming a central point in a sagittal plane through the patient's chest passing between the third and fourth electrodes when the housing is held adhesively secured against the patient's chest, wherein three orthogonal cardiac leads are formed from said electrodes and the central point; and a processor configured to process the three orthogonal cardiac leads, wherein the processor comprises a is configured to operate in a first mode and to measure the three orthogonal cardiac leads when a finger contact is detected on both the third electrode and the fourth electrode, and to operate in a standby mode when no finger contact is detected on both the third electrode and the fourth electrode.

Thus, described herein are electrocardiogram (ECG) sensing and review apparatuses and methods that may provide multiple single-channel acquisition, for detection of arrhythmia that may include a change in QRS axis or change in QRS width, and/or may distinguish an arrhythmia from an artifact. The "gold standard" for assessing cardiac rhythm abnormalities is 12-lead ECG or 12-lead Holter. The advantage of a standard 12-lead ECG is in the ability to assess rhythm, conduction, repolarization from multiple leads allowing diagnosis of cardiac structural, electrophysiologic, and metabolic abnormalities and drug effects.

Peer reviewed publications point out that within the first 24 hours of monitoring of any one of six arrhythmias (supraventricular tachycardia, AF/AFL, pause >3 s, AVB, ventricular tachycardia, or polymorphic ventricular tachycardia/fibrillation), the 12-lead Holter monitor detected about 17% more reportable events than a leading ECG patch technology. Other arrhythmias and conduction disorders most likely have been under-detected by ECG patches, likely owing to their single-lead nature compared with the 12-lead Holter monitor. Some ECG patches offer multiple electrodes that are attached to the chest only, however they offer diagnostic information that is still confined to a single signal plane. To achieve a 12-lead equivalency in terms of diagnostic content the patch described herein may record signals in all three human body cardinal axes: frontal, sagittal and transverse (X, Y and Z).

Cardiac electrophysiologic derangements often coexist with disorders of the circulatory system. Pathophysiologic states including current or pre-existing ischemia, infarction, left ventricular hypertrophy, and heritable arrhythmic disorders may also be revealed by a longer term (multiple week) monitoring. Post coronary artery disease intervention (stent or bypass surgery) patients at their discharge need monitoring to reassure them and to decrease unnecessary readmissions of these patients. Detection of coronary artery disease with a single lead ECG device is unreliable (poor accuracy) and because of that, single lead technologies are contraindicated for coronary artery disease detection. The methods and apparatuses may address these issues.

While not all occurrences of arrhythmia and other cardiac disorders are symptomatic majority of them are. The gold standard for diagnosing many rhythm disturbances is a symptom-to-ECG correlation. In practice that means that the patient who is wearing an ECG patch needs to mark somehow a symptomatic event. Usually, that is accomplished by a patient pressing a special "symptoms present" button typically located on the top surface of the patch (see, e.g., FIG. 12). In a way, this accomplishes an event monitoring function in an ECG patch. Usually, the whole multi-week recording is sent for analysis after the device is removed from the patient's chest.

For example, described herein are cardiac monitoring patch devices (e.g., an ECG patch for 12-lead detection) comprising: a casing having a front face and a rear face; two chest electrodes on the rear face separated for most orthogonal signal collection by about 5 cm and preferably by 10 cm or more; a first finger electrode and a second finger electrode on the front face; wherein the rear face comprises an adhesive configured to secure the two chest electrodes in contact with the skin; and a processor configured to detect when a first finger of the first hand contacts the first finger electrode concurrently with a second finger of the second hand contacting the second finger electrode, and to record electrical signals from the two chest electrodes and two finger electrodes.

In some examples the processor may be configured to automatically detect an ECG signal (e.g., a one-lead ECG signal) from the first electrode and the second electrode when the detection circuit does not detect the finger contact on both the third electrode and the fourth electrode. The processor may further be configured to detect an irregular cardiac signal from the detected ECG and in some examples may prompt the patient to touch the third electrode and the fourth electrode when the irregular cardiac signal is detected, and/or may prompt the patient to actuate a "symptoms present" control (e.g., button).

In general, described herein are adhesive patch apparatuses (devices, systems, etc.) for synthesizing a 12-lead electrocardiogram using four electrodes (two hands and two chest). For example, also described herein are adhesive patch devices for synthesizing a 12-lead electrocardiogram, the device comprising: a patch of adhesive material having a back and a front, wherein the back is configured to be adhesively secured to a patient's chest; a first electrode and a second electrode integrated on the back of the patch configured to measure bioelectric signals from the patient's chest, wherein the first and second electrodes are positioned a distance of at least 5 cm apart; a third electrode on the back of a right arm region of the patch and configured to measure bioelectric signals from the patient's right arm; a fourth electrode on the back of a left arm region of the patch and configured to measure bioelectric signals from the patient's left arm; a processing network forming a central point in a sagittal plane through the patient's chest passing between the third and fourth electrodes when the housing is held adhesively secured against the patient's chest, wherein three orthogonal cardiac leads are formed from said electrodes and the central point; and a processor within a housing on the patch configured to process the three orthogonal cardiac leads derived from the first, second, third and fourth electrodes. The processor may be configured to periodically process the three orthogonal cardiac leads from the first, second, third and fourth electrodes. In some examples, the processor may be configured to continuously process the three orthogonal cardiac leads from the first, second, third and fourth electrodes.

BRIEF DESCRIPTION OF THE DRAWINGS

FIG. 6A is a front (non-chest) view of the handheld device with electrodes on the edges of the device.

FIG. 6B is a back (chest) view of the handheld device with electrodes on the edges of the device.

FIG. 6C is an axonometric view of the handheld device with electrodes on the edges of the device.

FIG. 7 is an axonometric view of the handheld device realized as a flip case attachable to a mobile phone.

FIG. 8 shows a flow chart of the method for detecting AMI.

DETAILED DESCRIPTION

Figure 1A:
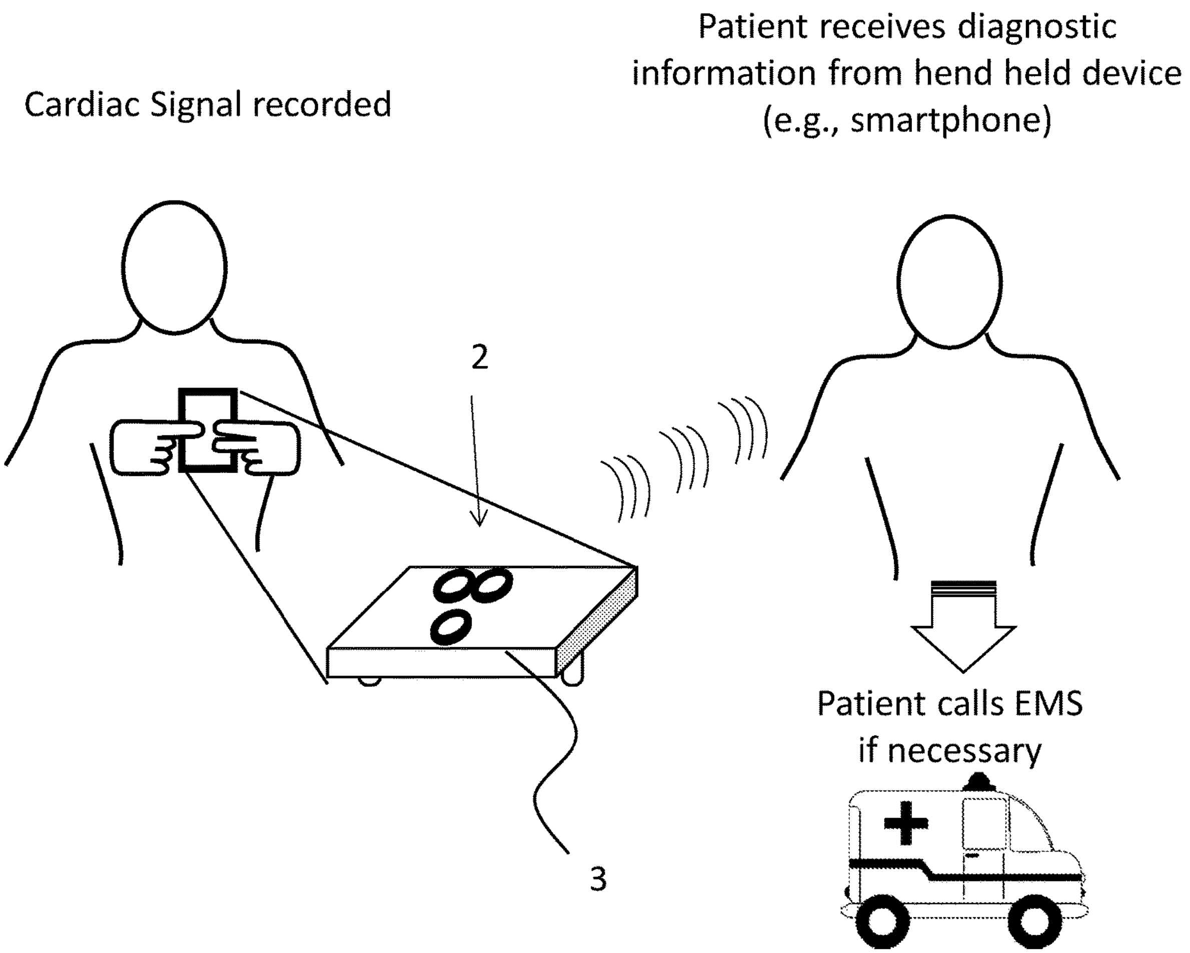
FIG. 1A shows one variation of a schematic configuration of a diagnostic system for detection of cardiac disorders such as AMI, including a local processor in the system.

Described herein are apparatuses (including devices and systems) and methods for remote diagnostics of cardiac conditions, such as acute myocardial infarction (AMI), atrial fibrillation (AFib), or the like. For example, described herein are handheld or hand-operated devices with special electrode configurations capable of recording three orthogonal cardiac lead signals in an orientation-specific manner, and transmitting these signals to a processor (e.g., PC or other computing device). In particular, described herein are adhesive cardiac devices that may be worn on the subject's chest for an extended period of time and operated by both of the subject's hands. The processor may be configured to diagnose/detect AMI and transmit the diagnostic information back to the handheld device and/or to the patient's (or a caregiver's) personal device (such as a phone, tablet, etc.). The handheld (and/or adhesively worn) device may communicate the diagnostic information to the patient via characteristic sounds, voice massages or via a graphical display. The processor may be configured via hardware, software, firmware, or the like, and may process the signals received to produce a difference signal and extract information reliably related to detection of AMI (and additional information of clinical relevance). Thus, these apparatuses and methods may perform automated detection of cardiac conditions on the basis of a 3-lead system, without the necessity for 12L ECG reconstruction, reducing or eliminating the need for medical personnel to interpret the ECG, unlike prior art systems, which typically rely on medical personnel for such decisions. The automated diagnostic methods described herein, in combination with the improved cardiac devices, address many of the needs and problems present in other systems.

Specifically, described herein are 3-lead cardiac recording devices for user placement on the chest, which include an arrangement of electrodes on both the front and back (and in some variations, one or more sides) so that the devices may be held by both of the user's hand in a predefined orientation, so as to record a 3 lead cardiac signals when held against the user's chest. In order to fulfill the above-described functions, in some examples the device (which may be handheld or adhesively applied/worn) may record three leads without using cables (e.g., may include only surface electrodes held or held against the body). Further, the resulting three leads are non-coplanar, and as close to orthogonal as possible. In some examples at least one electrode may be mounted on the front side of the device (opposite to the chest side), which may provide force to assist in holding device against the chest. Unlike prior art devices, there is no requirement for low, non-dipolar content, as the apparatuses and methods described herein do not require reconstruction of 12L ECG from the measured 3 leads.

The devices described herein are configured to be mechanically stable and allow good electrical contact with the chest and to may eliminate the need for switching of finger contacts. In some examples, the devices described herein may include five electrodes, e.g., four recording electrodes and one ground electrode. A device as described herein may include two chest electrodes which are the recording electrodes and may be located on the back side of the device (e.g., and in some examples may be adhesively coupled to the skin). In some examples the remaining non-chest electrodes may be used for collecting cardiac signals from the fingers of the right and left hand; in some examples a third one may be used as a ground electrode. At least one of these three non-chest electrodes may be mounted on the front side for pressing with the fingers. In some examples this may produce enough force to hold the device against the chest. In some variations the electrodes may be asymmetrically arranged; this asymmetric electrode configuration may prevent the need for identifying which finger/hands are used. For example, one of the three non-chest electrodes may establish contact with one finger of the first hand, and the remaining two electrodes may establish contact with the other hand. One of these two electrodes may be used as common ground electrode and the other may be used for signal measuring. An example of such configuration has two chest recording electrodes, one recording finger electrode on the left side of the device and two finger electrodes on the front side of the device, one recording and one ground electrode. In some examples, the optimal position of the device on the chest may be with the center of the device on the left side of the chest approximately above the center of the heart muscle. In this position, the chest electrodes may be approximately on the midclavicular line, the vertical line passing through the midpoint of the clavicle bone, same as for the V4 electrode of the conventional ECG, and the lower chest electrode is at about the level of the lower end of the sternum.

In another embodiment, the ground electrode may be excluded from the configuration, which may give acceptable 50-60 Hz electrical noise performance if a ground-free signal amplifier configuration is used. A four recording electrode configuration (having two chest and two finger electrodes) may also fulfill the condition of high orthogonality discussed above. The simplest way to fulfill this requirement is to record signals in three main body directions: lateral (left arm-right arm), sagittal (back-front) and caudal (head-toes). For example, the signal in the lateral direction may be obtained by measuring the lead between left and right hand. The signal in the caudal direction may be obtained by measuring the lead between the two chest electrodes, with the condition that the distance between the chest electrodes in caudal direction is at least about 5 cm, in some examples greater than about 10 cm, in order to be greater than the approximate diameter of the heart muscle. In an ideal case, the signal in the sagittal direction would be measured between the back and the chest of the patient, which is not possible with the constraint of using only finger and chest electrodes. To overcome this, we use a simple resistive network to make a central point (CP) that is close to the heart electrical center. For recording a lead in approximately sagittal direction, we record the voltage of the lower chest electrode with respect to a central point (CP), obtained using two hand electrodes and two resistors. The two resistors may be equal, approximately 5 kΩ each, or unequal, the first one approximately 5 kΩ between the left-hand electrode and the CP, and the second one approximately 10 kΩ between the right-hand electrode and the CP. This asymmetry reflects the left-side position of the heart in the torso, thus shifting the CP at the approximate electrical center of the heart. In this way we obtain a three lead system that are substantially orthogonal.

Other similar lead configurations with the same CP may be chosen using the same set of two chest and two hand electrodes, with the distance between the chest electrodes in caudal direction at least 5 cm, preferably greater than about 10 cm. Such a lead configuration may be substantially orthogonal, for example when both chest electrodes are used to record leads with the reference pole at the CP. Another possibility to define CP is using three electrodes, two hand electrodes and one chest electrode, and 3 resistors connected in a Y (star) configuration.

Other lead configurations without CP may also be used, like the configuration recording the signal of two chest electrodes and right-hand electrode with respect to left hand electrode. Such configurations without resistors or CP are more noise resistant to, for example, 50-60 Hz electrical noise, but have less orthogonal lead directions than the described ones using a CP. Generally, any other lead configuration using the same four described electrodes (a total of 20 configurations without a CP) results in leads that are non-coplanar and as such capture diagnostic signal in all three directions but may lack a high degree of orthogonality. However, these configurations may have different levels of orthogonality, depending on the use of the right-hand electrode. The configuration using the right-hand electrode as the common reference pole in all 3 leads may have the lowest orthogonality, since the right-hand electrode is farthest from the heart among the four electrodes, and thus the angles between the vectors corresponding to the three leads are the smallest. The configurations using right hand electrode in two leads have better orthogonality, while best orthogonality is achieved in the configurations using right hand electrode in only one lead.

The effectiveness of the described solution is not affected if one or more chest electrodes are added on the back side of the device, and one or more corresponding additional leads are recorded and used in diagnostic algorithms. Also, the effectiveness will not be affected if front electrodes are pressed with palms or any other part of hands instead with the fingers.

In order to prevent turning the device upside down during the recording procedure, so that the upper side is facing toes of the patient, instead of facing his head, which would lead to a useless recording, either upper or front side of the device may be clearly identified and/or formed, (including being marked) to be easily distinguishable by the patient, for example by a LED diode indicating the current phase of recording.

In some examples, the cardiac device (including either handheld or adhesively attached device configurations) may be configured as a stand-alone device incorporating an ECG recording module including amplifiers and AD convertor, data storage module, communication module operating on GSM, WWAN, or a similar telecommunication standard for communication with the remote processor (e.g., PC computer, pad, smartphone, etc.) and circuitry (e.g., Wi-Fi, Bluetooth, etc.) for communicating the diagnostic information to the user. Alternatively, it can be realized as a modified mobile phone that includes measuring electrodes and the recording module. Furthermore, it can be realized as a device that is attached to the mobile phone as a case or interchangeable back cover. The attached device incorporates measuring electrodes and the recording module and communicates with the mobile phone using a connector or a wireless connection such as Bluetooth or ANT.

If the device is configured as modified mobile phone or as a device attached to a mobile phone, the hand electrodes may be mounted on the display side of a mobile phone. The hand electrodes can be integrated in the edges of the display side of the phone, or as conductive areas incorporated in a transparent layer covering the display of the phone, arranged in the same way as hand electrodes in the preferred embodiment, and marked with a special color when a cardiac signal measuring application is active.

The signal processing and diagnostic software can also be run on the processor (e.g., microprocessor) including a processor integrated in the device, instead of running on a remote processor (e.g., PC computer). In this case, the communication of recorded information to the remote computer may no longer be required, except for data and processing backups. Also, when the diagnostic processing is carried out by a remote processor, a backup version of the software running on the microprocessor may be integrated in the device and may be used in situations when the user is in a zone without wireless network coverage.

Also described herein are methods and apparatuses for automated detection of AMI (or ischemia, the underlying physiological process). These automated systems may include three cardiac leads that are substantially orthogonal contain the majority of diagnostic information that is present in the conventional 12-lead ECG. Each user may be registered in the diagnostic system by performing the first transmission of his/her non symptomatic cardiac recording with 3 cardiac leads. This first recording may be used as a reference baseline recording for AMI detection in the diagnostic recording (diagnostic recording meaning any further recording of the 3 cardiac leads of the same user). The availability of the reference baseline cardiac recording may allow distinguishing new from old STE (or equivalent parameter), and also other cardiac signal changes suggesting an AMI, providing a tool for automated AMI detection that may have diagnostic accuracy comparable to human ECG interpreters.

The optimal placement of the devices (e.g., handheld and/or adhesive) described herein may be typically on the chest is with center of the device on the left side of the chest approximately above the center of the heart muscle. In this position, the right edge of the device may be about 3 cm away from the midsternal line, the vertical middle line of the sternum, and the lower edge of the device is at about level of the lower end of the sternum. In an ideal case, the user chooses the optimal position on the chest in the first baseline recording and repeats this position in each future diagnostic recording. In such situation, the cardiac recordings are repeatable, and it is easy to detect cardiac signal changes suggesting an AMI.

In some variations, an adhesive may be used to secure the device to the subject (e.g., patient's) chest, including for an extended period, such as days, weeks or months. Thus the apparatus may include an adhesive material, or an adhesive patch or dock may be used to connect to reproducibly connect to the apparatus and hold it in a predetermined position on the user. For example, the same recording position of the electrodes during the baseline recording and any further test recording can be achieved using a self-adhesive patch with (or connecting to a device with) the chest electrodes. A self-adhesive patch with the chest electrodes may be attached for the first recordings and remains on the same place on the user chest. Similarly, a patch to which the apparatus may dock to place the electrodes in a predetermined location may be used. The user needs to touch the hand electrodes.

In a realistic case, the user may place the device at a position that is different compared to the baseline position, which may compromise diagnostic accuracy. This misplacement is equivalent to a virtual change of the heart electrical axis in the 3D vector space defined by the 3 cardiac leads. In some variations, this angular change may be calculated for each test recording compared to baseline recording. If the angular change is greater than a threshold, such as 15 degrees, the user may be alerted to choose a position that is closer to the baseline position. If the change is lower than the threshold, it may be compensated for by rotating the signal loops of the test recording in the 3D vector space and get the signal that is substantially equivalent to the baseline signal.

Although switching of the left and right finger or turning the device upside down is not very likely (due to asymmetric electrode configuration and configuration of the apparatus, e.g., by clear marking of the upper or front side of the device), it may still be possible. In this case all three signals may become unusable. Both of these user errors may be easily detected, since in both cases the signal of the lead recorded between the left and the right hand may become inverted. In such case, the user may be alerted to repeat the recording using the correct recording position.

The method for automated detection of AMI (or ischemia) may, in some variations, the following steps: placing the device in a recording position on the user chest; acquisition of a first 3 lead cardiac recording and communicating the signals to the processing unit; storage of the first recording in the data base of the processing unit as baseline recording for further comparison with any subsequent diagnostic recording; acquisition of the 3 lead cardiac diagnostic recording and communicating the signal to the processing unit, and processing of the resulting signals. Processing of the stored baseline signals and signals of the diagnostic recordings by the processing unit may include the following steps: pre-processing to eliminate power line interference, baseline wandering and muscle noise, obtain representative beat using fiducial points and median beat procedure, check for switching of the left and right finger, beat alignment to bring baseline and test recordings' representative beats in the same time frame so as the corresponding points are synchronized, compensation for chest electrode mispositioning in recording the test signal by compensating the heart electrical axis deviation in the 3 cardiac leads vector space, calculating difference signal, representing the change between baseline and diagnostic 3 cardiac leads signals, detection of cardiac signal changes suggesting ischemia by comparing the parameters of the test recording to the baseline recording or by comparing parameters on the difference signal to a predefined threshold, communicating information by the processing unit to the device, and finally communicating the diagnostic information by the device to the patient.

The STE (ST segment elevation) is the most common ECG change in case of ischemia, usually measured at the J point or up to 80 msec later. Using STE as a parameter, the ischemic changes may be detected by comparing STE in the test recording to the baseline recording. Also, the ischemic changes may be detected by measuring the vector difference of the ST vector in the vector space defined by the 3 special cardiac leads (STVD), taking the baseline recording as a reference. As mentioned above, although these parameters (e.g., ST, J, STVD, STE), are defined with respect to traditional 12-lead ECG signals, they be herein refer to equivalent measures determined for the three cardiac leads (orthogonal signals) described herein. Thus, these equivalent points, regions or phenomena (e.g., STE, ST, J, STVD, etc.) may be identified by comparison between the cardiac signals described herein and traditional ECG signals, including traditional 12-lead ECG signals.

Other parameters of the ECG signal may also be used for comparison with the baseline reference signal, such the "Clew", defined as the radius of the sphere which envelopes the vector signal hodograph between J and J+80 msec points.

Cardiac signals for an individual are highly repeatable as far as their shape is concerned. The changes of the signal shape are generally small for a healthy, or an individual in stable condition. For example, the change of the position of the heart with respect to rib cage can change the heart electrical axis by up to 10°. However, there are conditions when the signal shape may change over time, like Benign Early Repolarization (BER). Such signal changes are highly individual and could be significant. To compensate for such changes, a number of baseline recordings, taken by the user over a period of time, may be used to form a reference that forms a 3D contour in the vector space defined by the 3 special cardiac leads (instead of a single point when single baseline recording is used). In using such a 3D contour reference, the ST vector difference (STVD) may be defined as a distance from the 3D contour instead from the baseline ST vector. If more than one parameter is used for ischemia detection, such a reference contour may be constructed as a hyper-surface in a multidimensional parameter space defined by such parameters. In this case a hyper-distance from the reference hyper-surface will be defined in the said parameter space.

In some conditions, the signal shape changes may also be intermittent (the condition "comes and goes"), like in Brugada syndrome, WPW syndrome, Bundle Branch Blocks (BBB), etc. To compensate for signal changes in such conditions, two groups of baseline recordings (e.g., at least two recordings) may be used to define the reference, one with normal signals and one with the said intermittent condition present. These two groups will form two 3D contours in the vector space, forming a reference for comparison. These two 3D contours may overlap or not. If there is no overlap, the ST vector difference (STVD) will be defined as a distance from closest point on the two 3D contours. If more than one parameter is used for ischemia detection, such reference contours would be constructed as two hyper-surfaces in a multidimensional parameter space defined by such parameters. In this case a hyper-distance from the reference hyper-surface will be defined in the said parameter space.

Primary use of the methods described herein may be applied to the detection of the most urgent cardiac diagnosis—the AMI. Additionally, the diagnostic methods (e.g., software) in the remote processor (or integrated processor in the handheld device) can detect other cardiac conditions such as chronic Coronary Artery Disease (CAD), Left Ventricular Hypertrophy (LVH), Bundle Branch Blocks (BBB), Brugada syndrome, rhythm disorders such as Atrial Fibrillation (AF) etc.

Although the methods described herein do not require the reconstruction of conventional 12 lead ECG recordings, they may be used to reconstruct them. In many of the above-mentioned conditions to be detected, treatment may be urgently needed, although to a lesser extent compared to AMI. Also, many of such conditions are transient, and may be detected using here described technology, but may not be present when the user later comes to the physician's office. In such a case, it would be useful to present the ECG signals for the condition that was discovered at the time of recording, so that physician may use it to confirm the diagnosis. Physicians are familiar with the conventional 12 lead ECG recording. Therefore, 3 special cardiac leads recorded when the condition was discovered may be transformed to produce an approximate reconstruction of conventional 12 lead ECG recording. Such reconstruction may be obtained by multiplication of the 3 special cardiac leads with a 12×3 matrix. This matrix may be obtained as a population matrix, that is a matrix with coefficients that are calculated as average, or median, values of individual matrices obtained by simultaneously recording conventional 12 lead ECG and 3 special cardiac leads in a population of individuals, with each individual matrix obtained using least squares method. The coefficients of such matrices are dependent of the shape of the user's body. Therefore, instead of using a single population matrix, multiple matrices may be used, each for a group of users defined by simple parameters of the body shape and structure, like gender, height, weight, chest circumference, etc., that may be easily obtained by the user. Also, matrix coefficients may be obtained as continuous functions of such body parameters.

Figure 1B:
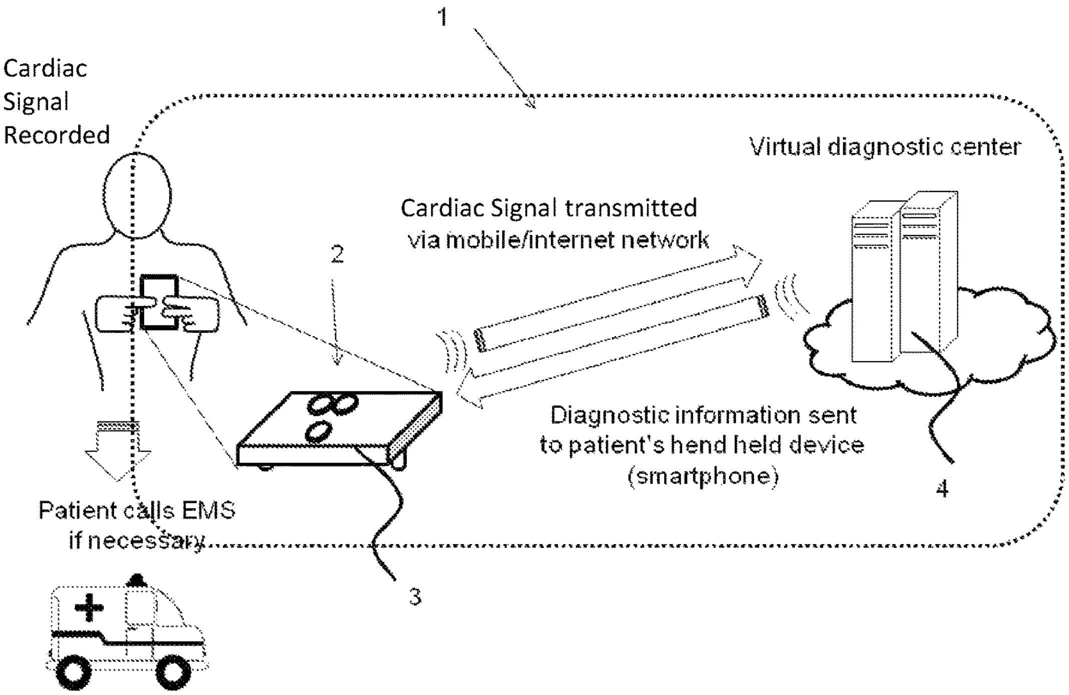
FIG. 1B is another schematic of a remote diagnostic system, wherein the processor is remote from the hand-held device.

FIG. 1A illustrates one variation of a method of operating a system 2 for cardiac signal detection and/or diagnosis. In FIG. 1A, the user may record cardiac signals (e.g., at two or more times), and the apparatus may process the three orthogonal leads to compare the different times (e.g., baseline vs. assay time). The processor of the apparatus may further determine if the resulting differential signal indicates that cardiac problem and can alert the user. The user (patient) can then get medical assistance as necessary. FIG. 1B shows a view of anther variations of a system and method for detecting cardiac dysfunction, including a system 1 for remote diagnostics of AMI including handheld device 2 incorporating built in electrodes for cardiac signal acquisition, mounted directly on the casing 3 of the handheld device and a PC computer 4 connected via a telecommunication link to the device.

The device further incorporates a cardiac signal recording circuitry including amplifiers and AD convertor for amplifying the signals detected by the electrodes, data storage (e.g., memory) for storing the recording signal, communication circuitry operating on GSM, WWAN, or a similar telecommunication standard for communication with the remote processor 4 and visual and/or audio (e.g., monitor, speaker, etc.) for communicating the diagnostic information to the user.

The device may be communicating with the remote processor 4 via integrated communication circuitry. The remote processor 4 may communicate with the handheld device 2 via integrated communication module. The processor 4 may be equipped with diagnostic software for processing the received cardiac signals, producing diagnostic information and for transmitting the information back to the handheld device for communicating the diagnostic information to the patient via microphone producing characteristic sounds or voice messages or in the form of graphical information via a display integrated in the device. As a consequence, the system may be capable of performing automated detection of a cardiac condition on the basis of a 3-lead system and doesn't require interpretation of the processed diagnostic information by a specialist. Alternatively, instead of a remote processor, the system may include a microprocessor integrated in the casing 3 of the handheld device for processing the recorded cardiac signals and producing diagnostic information.

Figure 2A:
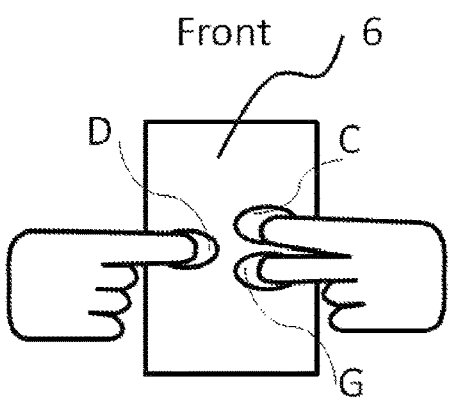
FIG. 2A shows a front (non-chest) view of one variation of a handheld device with two recording and one ground electrode.
Figure 2B:
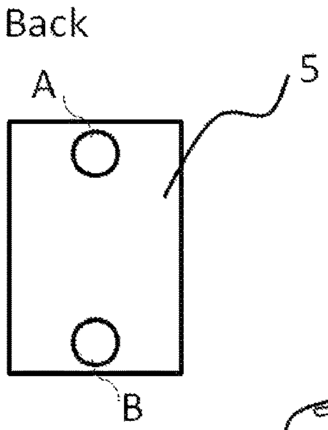
FIG. 2B shows a back (chest) view of one variation of a handheld device with two recording electrodes.
Figure 2D:
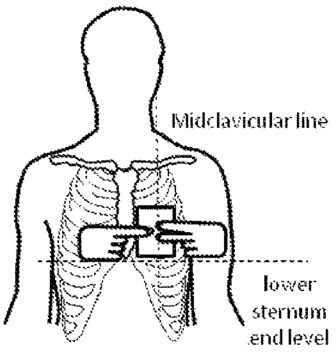
FIG. 2D shows a front view of the device placed against the patient's body in a recording position.
Figure 2C:
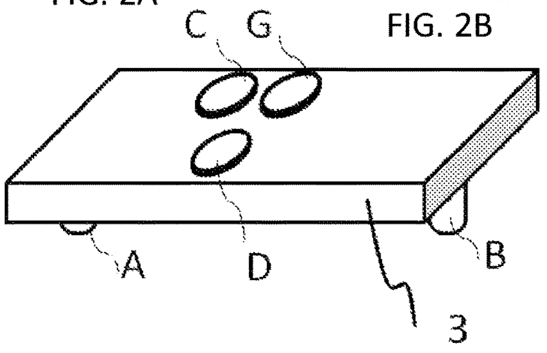
FIG. 2C shows an axonometric view of a handheld device.

FIGS. 2A, 2B and 2C show front, back and axonometric views, respectively, of an example of a handheld device. FIG. 2A shows the front view of the device 2 in the recording position as held by the user. The casing 3 of the device may incorporate four recording electrodes A, B, C, D, and one ground electrode G arranged in such arrangement that enables recording of three special ECG lead signals. On the flat back surface 5 of the device in this example are mounted two recording electrodes, A and B, used to make contact with the chest of the patient in the recording position. The two chest electrodes, A and B, are preferably arranged to cover distance greater than at least 5 cm, preferably greater than about 10 cm in caudal direction. The reason for having such spaced arrangement is to achieve the distance greater than approximate diameter of the heart muscle which is needed to approach as much as possible lead orthogonality.

In addition to the two chest electrodes, A and B, the device in this example has two recording electrodes, C and D, mounted on the flat front surface 6 substantially parallel and opposite to the back surface 5. These electrodes, C and D, are used for recording cardiac signals of the hands by pressing with fingers of the left and right hand respectively. The fifth electrode G serves as grounding electrode and is mounted on the front surface 6 for pressing with a left-hand finger.

Referring back to FIG. 2A, there is shown a view of the preferred embodiment of the invention in recording position. For operation, the user (e.g., patient) places the device in his left hand so that patient's index and middle finger contact electrodes C and G respectively, positions and presses the device against his chest so that the chest electrodes A and B contact his chest in the manner shown in FIG. 2E for producing tight contact between chest and the device. This may produce enough pressure for holding the device against the chest. Simultaneously, a finger of the right hand (or any other part of the right hand) presses the reference electrode D mounted on the front surface 6 of the casing 3.

Referring back to FIG. 2D there is shown a front view of the device placed against the patient's body in recording position according to the preferred embodiment of the invention. In an optimal recording position the center of the device is placed closely above the center of the heart so that the chest electrodes A and B are approximately on the midclavicular line (the vertical line passing through the midpoint of the clavicle bone), and the lower chest electrode B is at about the level of the lower end of the sternum.

Figure 3A:
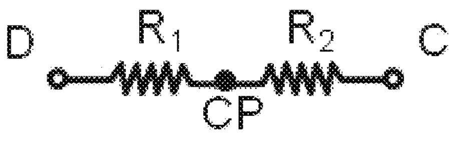
FIG. 3A shows a simple electrical scheme for obtaining a central point CP by connecting the electrodes of both hands via a simple resistive network with two resistors.
Figure 3B:
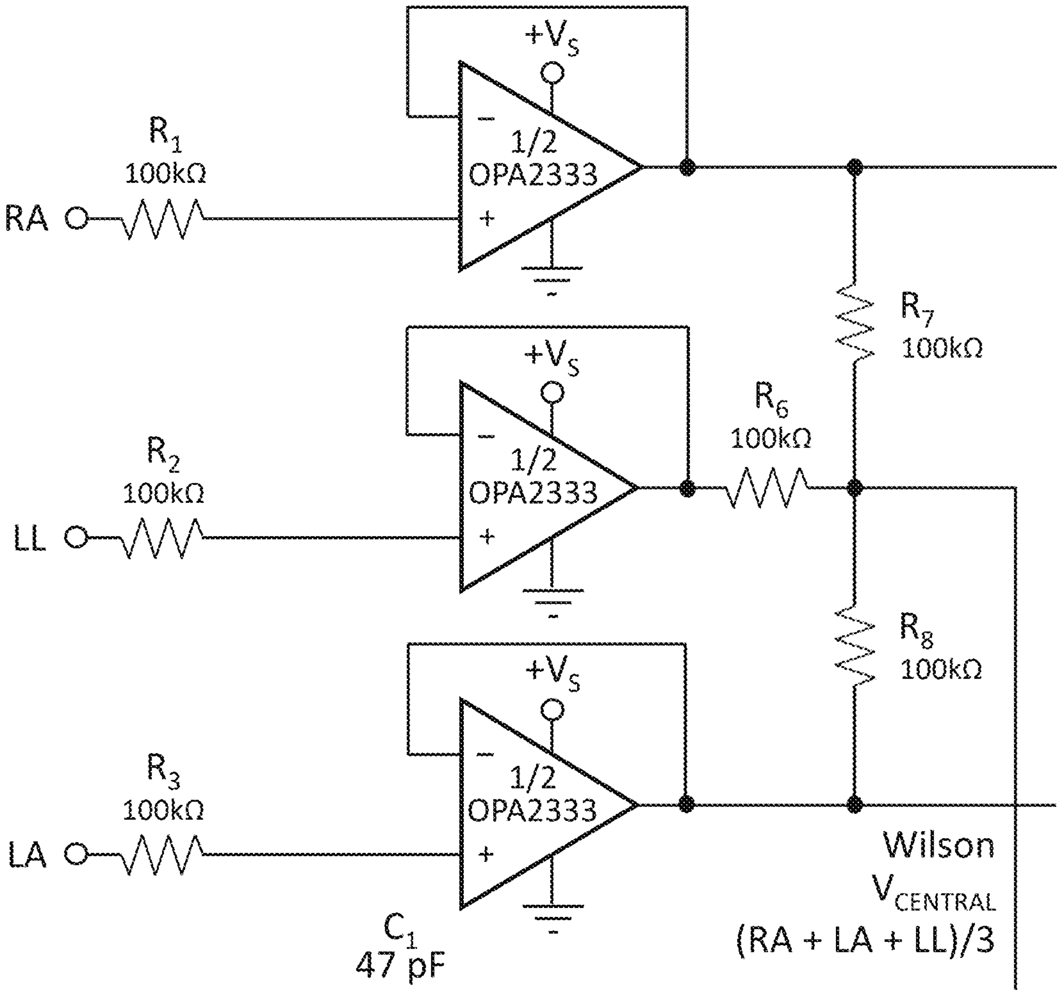
FIG. 3B shows an electrical scheme for obtaining a central point CP by averaging electrode signals via known operational amplifier (op amp) configurations.

The example in FIG. 3A shows a simple electrical scheme for obtaining a central point CP by connecting the electrodes of both hands via a simple resistive network with two resistors. Similarly, FIG. 3B shows an electrical scheme for obtaining central point CP using buffering and averaging via operational amplifiers.

Figure 4A:
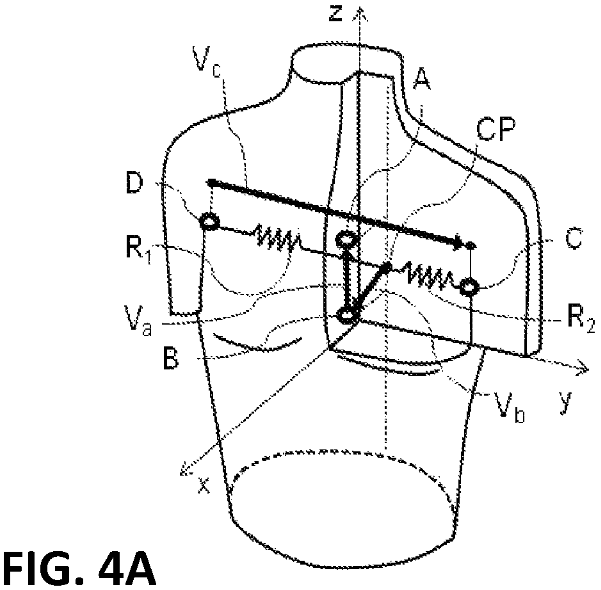
FIG. 4A shows schematic configuration of the three cardiac leads measured on the torso with one lead using central point as the reference pole—the preferred embodiment.

FIG. 4A shows a spatial view of the lead configuration according to one embodiment, illustrating the arrangement of active electrodes A, B, C, D with respect to the body, as well as relative arrangement between the electrodes. FIG. 4B shows a simplified electrical scheme illustrating the same relative arrangement between the electrodes shown in FIG. 4A. For recording a lead in approximately sagittal direction, the voltage of the lower chest electrode B with respect to a central point CP may be obtained using the hand electrodes C, D and two resistors R1, R2. The two resistors R1, R2 can be equal, approximately 5 kΩ each, or unequal, approximately 5 kΩ between the left-hand electrode and the CP, and 10 kΩ between the right-hand electrode and the CP. This asymmetry may reflect the left-side position of the heart in the torso, thus putting the CP point at the approximate electrical center of the heart. In this way a substantially orthogonal three lead configuration may be obtained.

Figure 4C:
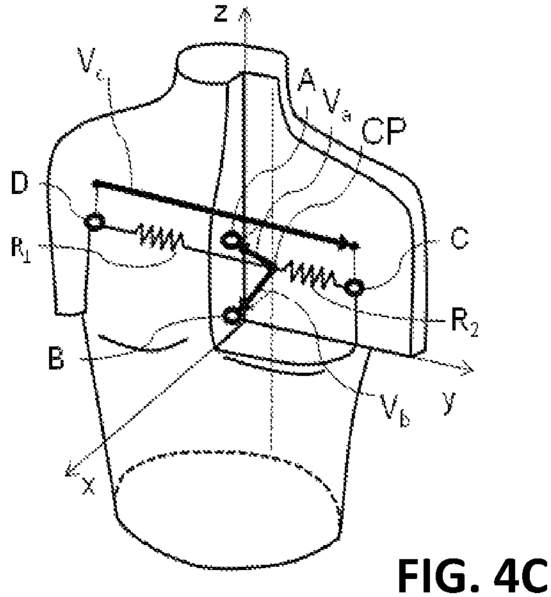
FIG. 4C shows a schematic configuration of the three cardiac leads measured on the torso with two leads using central point as the reference pole.
Figure 4B:
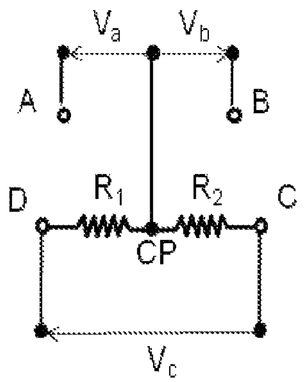
FIG. 4B shows an electrical circuit of the three cardiac leads with one lead using central point as the reference pole.
Figure 4D:
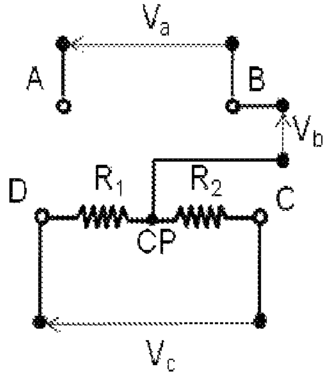
FIG. 4D is an electrical circuit of the three cardiac leads with two leads using central point as the reference pole.

FIG. 4C shows a spatial view of an alternative lead configuration with the central point CP using the same set of chest and hand electrodes A, B, C, D, illustrating arrangement of the electrodes with respect to the body, as well as relative arrangement between the electrodes. FIG. 4D shows simplified electrical scheme illustrating the same relative arrangement between the electrodes A, B, C, and D, shown in the FIG. 4C. This alternative lead configuration using a central point CP and measuring two leads between the CP and each of the chest electrodes is also substantially orthogonal, since the chest electrodes A, B are used to record leads with the reference pole at the CP which is obtained using two hand electrodes C, D and two resistors R1, R2.

Figure 4E:
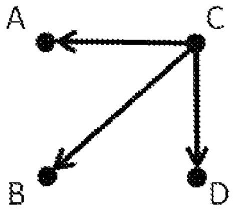
FIGS. 4E, 4F and 4G show schematic diagrams of three possible configurations for measuring 3 leads among two chest and two hand electrodes.
Figure 4F:
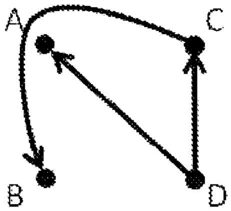
Figure 4G:
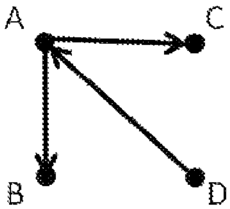

Other lead configurations without central point CP and resistors may also be used, like the configuration shown in FIG. 4E, recording the signal of two chest electrodes and right-hand electrode with respect to left hand electrode. Other two similar configurations are shown in FIGS. 4F and 4G. Such configurations without resistors are subject to less external interference, such as 50-60 Hz electrical noise, but have less orthogonal lead directions than the previously described ones using a CP. Generally, any other lead configuration using the same four described electrodes may result in non-coplanarity and, as such, captures the diagnostic signal in all three directions, but lacks high orthogonality. There are a total of 20 possible configurations without a CP, including ones shown in FIGS. 4E, 4F and 4G. However, these configurations have different levels of orthogonality, depending on the use of the right-hand electrode. The configuration using the right-hand electrode as the common reference pole in all 3 leads have the lowest orthogonality, since the right-hand electrode is farthest from the heart among the four electrodes, and thus the angles between the vectors corresponding to the three leads are the smallest. The configurations using right hand electrode in two leads, such as the configuration shown in FIG. 4F, have better orthogonality, while best orthogonality is achieved in the configurations using right hand electrode in only one lead, such as the configurations shown in FIGS. 4E and 4G.

Figure 5A:
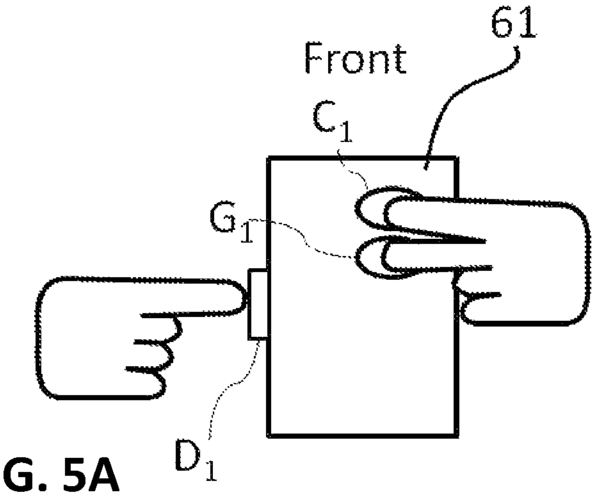
FIG. 5A shows a front (non-chest) view of the handheld device with two front and one side electrode.
Figure 5B:
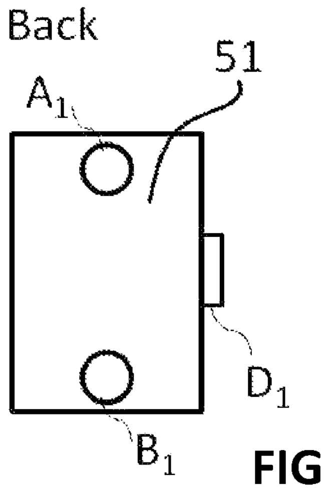
FIG. 5B shows a back (chest) view of the handheld device with two front and one side electrode.
Figure 5C:
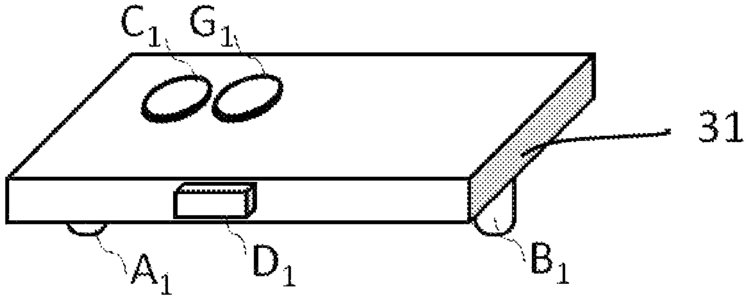
FIG. 5C shows an axonometric view of the handheld device with two front and one side electrode.
Figure 9:
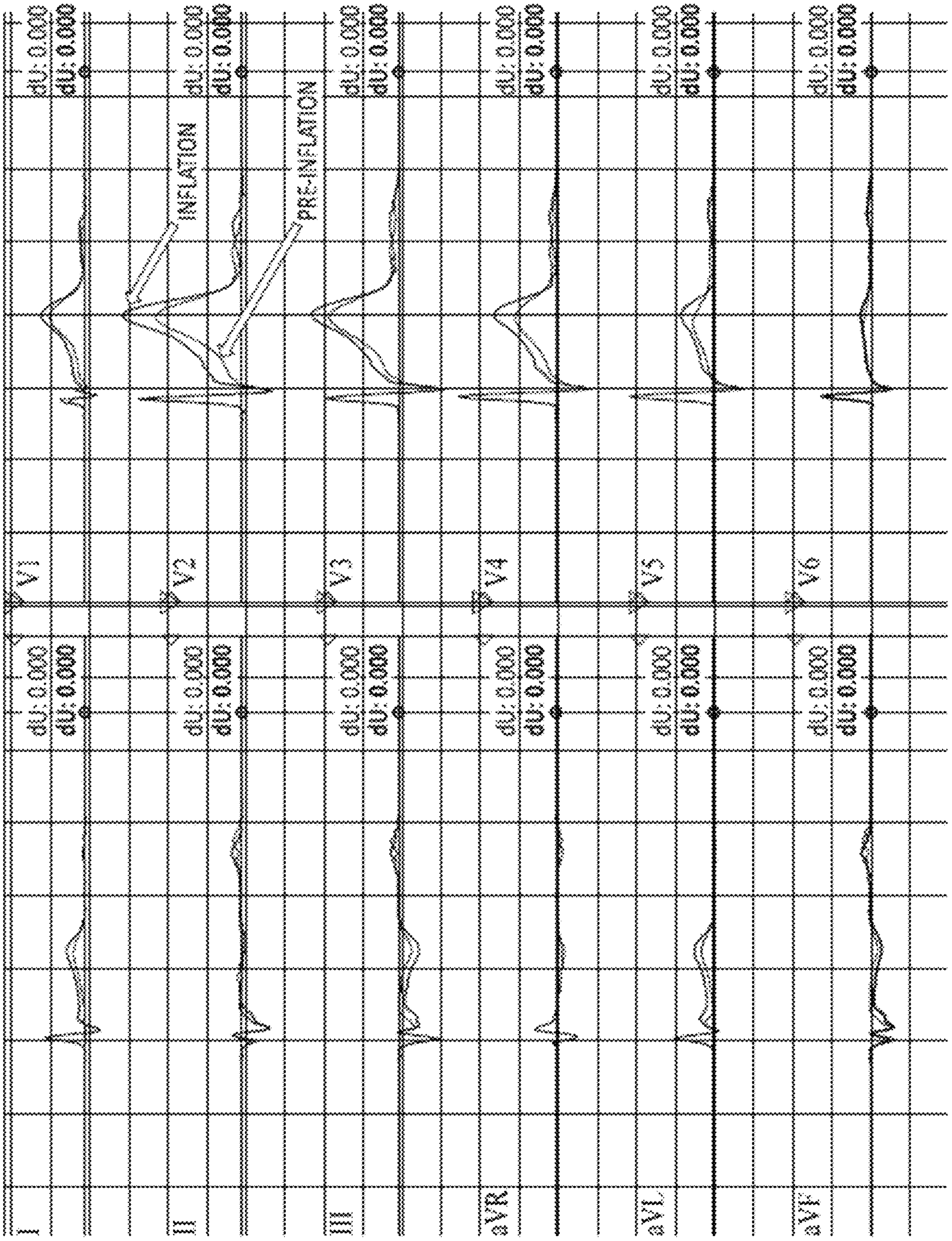
FIG. 9 shows one example of a patient with BER (Benign Early Repolarization), showing median beats in 12 leads. Both pre-inflation and inflation recordings show ST segment elevation in precordial leads, which is typically problematic for a human reader to distinguish ischemic from non-ischemic recording.
Figure 10:
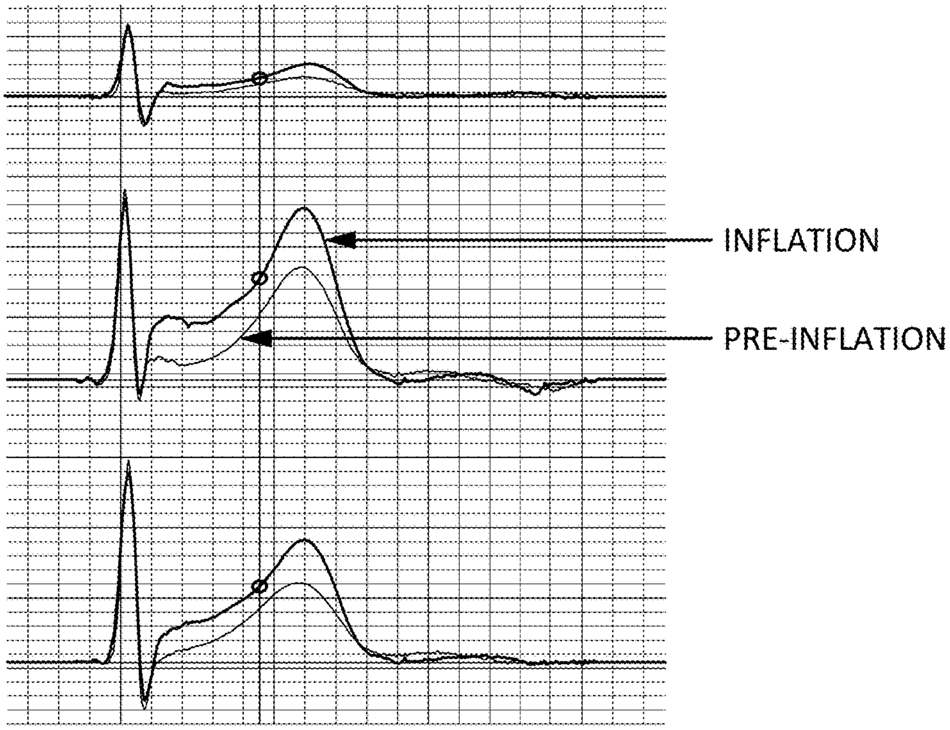
FIG. 10 is an example of a patient with BER (Benign Early Repolarization), showing median beats in 3 special leads. The signal difference between pre-inflation and inflation recordings enables the algorithm to distinguish ischemic from non-ischemic recording.
Figure 11:
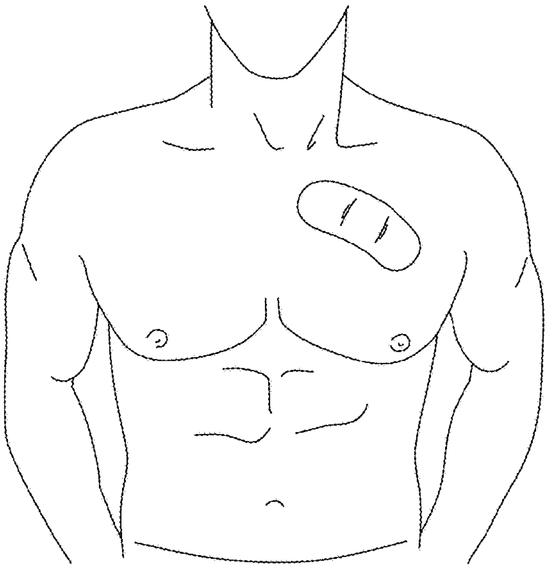
FIG. 11 illustrates one example of a typical ECG patch size and placement: two adhesive chest electrodes are positioned about 10 cm apart for single lead ECG recording.

FIGS. 5A, 5B and 5C show front view, back view and an axonometric view, respectively, of an alternative embodiment of a handheld device, whereby FIG. 5A shows the front view of the device in the recording position as held by the user. In the alternative embodiment, the electrode D1 for recording ECG signal of the right arm by pressing with finger of the right hand is mounted on the flank 71 of the casing 31, instead on the front surface 61 as in the embodiment described above. Active recording electrodes A1 and B1 for recording ECG signal of the patient's chest are mounted on the back surface 51 of the device in the same manner as in the embodiment above. An active recording electrode C1 for recording ECG signal of the left hand by pressing with finger of the left hand and ground electrode G1 for pressing with another finger of the left hand are mounted on the front surface 61 also in the same manner as above.

The finger switching may be prevented by having an asymmetric electrode configuration, so that the right-hand electrode cannot be wrongly pressed by the left hand, and vice versa. However in each of the embodiments (preferred and alternative), the upper (facing head) and lower part (facing toes) of the device may be easily distinguished, since turning the device upside down would lead to wrong recording. This may be done by integrating LED diodes in either upper or front side of the device, indicating the current recording phase, in the front surface of the device casing.

The cardiac devices described herein (e.g., handheld, adhesive, etc.) may be realized as a stand-alone device incorporating an ECG recording circuitry including amplifiers and AD convertor, data storage circuitry (memory), communication circuitry operating on GSM, WWAN, or a similar telecommunication standard for communication with the remote PC computer and an output for communicating the diagnostic information to the user (e.g., screen, speaker, etc.). In so embodiments, the apparatus may be configured to operate with a modified mobile phone that includes measuring electrodes and the cardiac signal recording capability. Furthermore, the apparatus can be realized as a system that is attached to a mobile phone (smartphone) as a case or interchangeable back cover. The attached device may incorporate measuring electrodes and the cardiac signal recording module (including electrodes, balancing circuit, etc.) and communicates with the mobile phone using a connector or a wireless connection such as Bluetooth or ANT.

FIGS. 6A, 6B and 6C show a front view, back view and axonometric view, respectively, of another alternative embodiment of the handheld device. On the back side 52 of the device there are electrodes A2, B2 are mounted for touching the chest of the patient conducting the recording in the same manner as in the preferred embodiment. On the front side 62 of the device there are three electrodes, an active electrode C2, a reference electrode D2 and a ground electrode G2. All three electrodes C2, D2 and G2 have elongated, beam or band like shape and are integrated on the front side 62 of the device, preferably along the two longer, parallel edges of the housing 32 so as to be partially accessible from the sides. In the recording position, the electrodes C2, D2 and G2 are touched by fingers of the left and right hand, in the manner equivalent to the one shown for electrodes C, D and G shown in FIG. 2A, respectively. This electrode arrangement is suitable if the device is realized as a modified mobile phone that includes measuring electrodes and the cardiac signal recording module, or if it is realized as a device that is attached to the mobile phone as a case or interchangeable back cover. In such embodiment, the elongated electrodes may be a part of the frame surrounding the display of the mobile phone or tablet.

In some examples, the alternative electrode arrangement, featuring two electrodes on one side and on electrode on the opposite side, also fulfills the requirement of asymmetry avoiding the necessity for finger switching.

In another alternative example, the device is a modified mobile phone that includes recording electrodes and the cardiac signal recording module, with a touch screen. The three hand electrodes for pressing with hands or fingers are realized as transparent conductive areas incorporated in a transparent layer covering the display of the phone, arranged in the same way as hand electrodes in the preferred embodiment. The smart phone application will mark the conductive areas on the screen with a special color when the cardiac signal recording application is active.

In another alternative embodiment, the device contains self-adhesive patch with the chest electrodes. The self-adhesive patch is attached on the user chest enabling the same chest electrode positions for the baseline and all subsequent diagnostic recordings as described above. Alternatively or additionally, the apparatus (e.g., system) may include a patch having a docking region for connecting with any of the electrode-including devices described herein, that may be used to connect (or provide fiduciary reference for) the device to the same location on a user's chest. For example, a docking adhesive patch may include a mating component or region that connects to the device to hold the chest electrodes on the device in a reproducible location on the user's chest. In some variations, the docking adhesive comprises a Band-Aid type material that is worn by the user over an extended period of time (e.g., hours, days, weeks), and may be replaced with another adhesive to maintain the same reference location.

FIG. 7 shows another embodiment of the device realized as an extension 83 to a mobile phone, such as a case or interchangeable back cover, having a form of a so-called flip case or wallet for mobile phone, incorporating chest electrodes A3 and B3 on the back side of the device, and the left- and right-hand finger electrodes C3, D3 and G3 incorporated in the flip-type phone display cover 93 of mobile phone casing.

FIG. 8 shows a block diagram of the method for automated detection of AMI according to the preferred embodiment of the invention. A method for automated detection of AMI (or ischemia) may include all or some of the steps described below. First, placing the device in a recording position on the user chest.

An optimal position of the device on the chest is with center of the device on the left side of the chest approximately above the center of the heart muscle. In this position, the chest electrodes are approximately on the midclavicular line, the vertical line passing through the midpoint of the clavicle bone, same as for the V4 electrode of the conventional ECG, and the lower chest electrode is at about the level of the lower end of the sternum. The user presses one active electrode and one ground electrodes with the fingers of the left hand and one active electrode with the finger of the right hand on the front side of the device.

The method may also include acquisition of a first 3 lead cardiac recording and communicating the signals to the processing unit. The user of the automated AMI diagnostic system may perform the recording of the 3-lead cardiac signal by holding the device against the chest for a short period of time (e.g., at least 30 seconds, at least 20 seconds, at least 10 seconds, at least 5 seconds, etc.). The recording is stored in the memory of the device and then transmitted to the remote PC computer via commercial communication network.

The method may also include storage of the first recording in the data base of the processing unit as a baseline. After performing the first transmission of his/her cardiac signal, the cardiac signal recording is stored in a remote processor, and the user may be registered in the diagnostic system. Before this first transmission, the user or his MD/nurse may enter (via a dedicated web site) his medical data such as age, gender, risk factors for cardiovascular disease, etc., and indicate if he/she is currently having chest pain or any other symptom suggesting ischemia. If the answer is negative, this first cardiac recording is kept in the diagnostic system as a baseline recording that will serve as a reference for comparison in any further transmission when symptoms suggesting ischemia may occur.

The method may further include acquisition of the 3-lead cardiac diagnostic recording and communicating the signal to the processing unit. Any subsequent recording after the baseline recording has been accepted and stored in the data base is considered to be diagnostic recoding. The user of the automated AMI diagnostic system performs the diagnostic recording of the 3-lead cardiac signal by holding the device against the chest for at least 10 seconds. The diagnostic recording is stored in the memory of the device and then transmitted to the remote PC computer via commercial communication network.

In general, the methods described herein may include processing of the stored signals of baseline and diagnostic recordings by the processing unit. Processing may include pre-processing. For example the apparatus/method may be configured to let Va, Vb, Vc be the 3 special leads recorded using the device. Before performing any analysis, cardiac signal must be "cleaned" from the disturbing factors like power line interference, baseline wandering and muscle noise. While the former two may be removed using standard adaptive filtering and cubic spline techniques, respectively, the latter is suppressed using time-averaging median beat procedure.

To create a median beat, the entire cardiac signal may be delineated, resulting in set of fiducial points $S=\{P_1, P_2, \ldots, P_n\}$, where $Pi=\{Q_i, R_i, J_i, T_i, T_{i,end}\}$ (or points equivalent to these locations) are fiducial points of i-th beat. Based on S, the signal is then divided into n individual beats of the same length. Finally, individual beats are synchronized using cross-correlation (CC) and for each sample median value across all n beats is calculated. Thus, the entire cardiac signal is represented by the single most-representative median beat. A set of fiducial points $P=\{Q, R, J, T, T_{end}\}$ associated to the median beat are simply calculated as median values of the fiducial point of the individual beats.

Techniques for obtaining representative beat other than median beat may also be used. The delineation of the cardiac signal resulting in fiducial points for each beat may be done using different techniques like wavelet transform, support vector machine, etc.

The same pre-processing procedure is used for both baseline and diagnostic recording.

If the lead recorded between the left and the right hand, or other lead capturing the signal in the lateral direction, is inverted, the user is alerted to repeat the recording using the correct recording position.

The processing may also include beat alignment. For example, the apparatus or method may be configured to let B and D denote to the median beats extracted from the baseline and diagnostic ECGs, respectively, and PB and PD are their associated fiducial points. The goal of beat alignment is to bring B and D in the same time frame so as the corresponding points are accurately synchronized. This involves finding of such transformed B, referred to as B*, so that it is optimally synchronized to the D. The applied transformation is piece-wise uniform re-sampling of B, so that corresponding segments in B* and D, defined by PB and PD, respectively, have the same number of samples. Optimal alignment is obtained by searching for such fiducial points PB* that optimize cost function or similarity measure (SM) which quantifies the alignment:

$$P_B^* = \underset{P_B}{\arg opt} SM \tag{1}$$

B* is then obtained by transforming B using the $P_B$*.

In the present embodiment, we used CC which is commonly used SM for shape-based alignment problems. However, use of solely CC may lead to wrong alignment as shape in B and D may be significantly different. Therefore, we introduce weighting functions $f_{wi}$, which penalizes large deviations from the $P_B$, as the fiducial points $P_B$ are assumed to be accurately known:

$$f_{wi} = e^{-\left(\frac{\Delta P_{Bi}}{ci}\right)^2} \tag{2}$$

where i=Q, R, J, T, $T_{end}$, $\Delta P_{Bi}$ is deviation from the i-th fiducial point and ci is scaling factor which depends on the fiducial points. Namely, as the R point is the most stable reference in ECG signal, its deviation is penalized the most. On the other hand, as J and $T_{end}$ points are the least stable, thus, larger deviations are allowed. The overall SM is then calculated as product of CC and sum of weighting functions $f_{wi}$:

$$SM = CC(B(P_B), D)\sum_{i=1}^{5} f_{wi}(|P_B - P_{Bi}|) \tag{3}$$

Finally, according to the Eq. (1) the B* is obtained by finding optimum of SM given in Eq. (3).

The processing may also include compensation for chest electrode mispositioning. During regular use of the handheld device, chest electrodes may not be placed on the same spot every time, thus leading to changes in shape of cardiac signal even in absence of any pathology. This change can be modeled as "virtual" heart electrical axis deviation in the Va,Vb,Vc leads vector space if lead positions are assumed to be constant, with the heart electrical axis represented by the R vector—the heart vector at the moment of maximal magnitude in the QRS complex (or equivalent region in the three-lead cardiac signals described herein). However, this is undesired property as the difference signal ΔD will be significant, even though there are no pathologically induced changes. To overcome this problem, we transform D, resulting in D*=TD, so that its heart electrical axis overlaps with the axis of B*. The transform T is calculated using least squares method and Q-J segment (QRS complex) of D and B* as input.

In general, processing may also include calculating difference signal, representing the change between baseline and diagnostic3 cardiac leads signals. The difference signal ΔD*is calculated as:

$$\Delta D^* = D^* - B^* \tag{4}$$

Ultimately, such difference signal ΔD* will reflect solely pathologically induced changes and it will be independent on heart axis deviation.

Since the quality of the device misplacement compensation decreases with increase of the angle heart axis deviation, if the angular change is greater than a threshold, such as 15 deg, the user is prompted to choose a position that is closer to the baseline position.

The processing methods and apparatus described herein may also include detection of ischemic changes. The STE is the most common ECG change in case of ischemia, measured usually at the J point or up to 80 msec later. In the present solution, the ischemic changes are detected by comparing the test recording to the baseline recording. In the preferred embodiment, the parameter or "marker" for ischemia detection is STVM (or equivalent region in the cardiac signals described herein), the vector magnitude of the corrected difference signal ΔD* at 80 msec after the J point (J+80 msec), compared to a predefined threshold, such as 0.1 mV.

In other embodiments, vector magnitude in other time points may be used as marker for ischemia, such as J point, J+60 msec, T max, etc. Other markers may be used that describe the shape of the ST segment (ECG signal segment between J and J+80 msec points, or similar). Such a marker is the "Clew", defined as the radius of the sphere which envelopes the vector signal hodograph between J and J+80 msec points. Also, other composite markers may be used, such as a logistic regression using a linear combination of STVM and Clew markers.

To compensate for signal shape change over time, a number of baseline recordings, taken by the user over a period of time, may be used to form a reference that forms a 3D contour in the vector space defined by the 3 special cardiac leads (instead of a single point when single baseline recording is used). In using such a 3D contour reference, the ST vector difference (STVD) will be defined as a distance from the 3D contour instead from the baseline ST vector. If more than one parameter is used for ischemia detection, such a reference contour would be constructed as a hyper-surface in a multidimensional parameter space defined by such parameters. In this case a hyper-distance from the reference hyper-surface will be defined in the said parameter space.

In users having cardiac condition with intermittent signal shape changes, compensation for such changes may be done by forming two groups of baseline recordings (at least two recordings) to define the reference, one with normal signals and one with the said condition. These two groups will form two 3D contours in the vector space, forming a reference for comparison, and the ST vector difference (STVD) will be defined as a distance from closest point on the two 3D contours. If more than one parameter is used for ischemia detection, such reference contours would be constructed as two hyper-surfaces in a multidimensional parameter space defined by such parameters. In this case a hyper-distance from the reference hyper-surface will be defined in the said parameter space.

Any of these methods and apparatuses may be configured for communicating information by the processing unit to the device. The created diagnostic information may be transmitted from the remote processor (e.g., a PC computer, server, etc.) to the device memory via commercial communication network. The method and apparatuses may also be configured for communicating the diagnostic information by the device to the patient. The received diagnostic information may be presented to the user in a form of characteristic sound, voice, graphics or text.

Additionally, an approximate conventional 12 lead ECG signal may be sent to the user's physician for evaluation. This signal may be produced as an approximate reconstruction of conventional 12 leads by transforming the 3 special cardiac leads signals recorded by the user. This reconstruction may be obtained by multiplication of the 3 special cardiac leads with a 12×3 matrix. In one embodiment, this matrix may be obtained computationally by using a general solution of potentials distribution on the surface of the human body, similar to those previously described for defining a conventional vector cardiogram. In another embodiment, this matrix may be obtained as a population matrix, that is a matrix with coefficients that are calculated as an average, or median, values of individual matrices obtained by simultaneously recording conventional 12 lead ECG and 3 special cardiac leads in a population of individuals, with each individual matrix obtained using least squares method. In yet another embodiment, multiple matrices may be used in corresponding user groups defined by simple parameters of the body shape and structure, like gender, height, weight, chest circumference, etc., that may be easily obtained by the user. Also, matrix coefficients may be obtained as continuous functions of such body parameters.

Adhesive Devices

As described above, any of the apparatuses (e.g., devices) described herein may be configured to be adhesively secured to a subject (e.g., patient) and may include two or more electrodes on the adhesive side as well as two or more finger electrodes arranged as described above (similar or identical to the handheld examples). These apparatuses may include an of the features of the handheld devices described. These adhesive devices may also or alternatively be referred to as "patch" devices. Thus, the devices and systems described herein may include ECG patches configured to receive and process 12-lead ECG information that may be used to detect cardiac conditions. These ECG patches may be worn for long periods of time (e.g., more than 24 hours).

Figure 14:
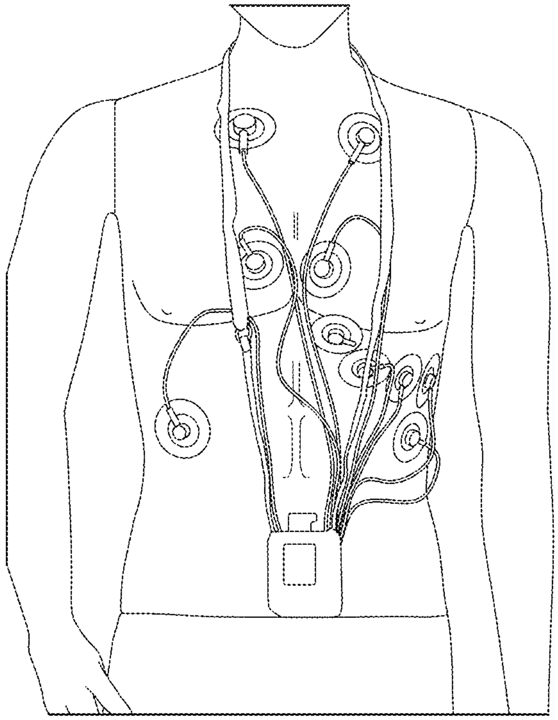
FIG. 14 illustrates one example of a 12-lead Holter ECG monitor.

The ECG patches described herein addresses key limitations of prior art. As described above, 12-lead ECG is diagnostically superior to a single lead ECG for most cardiac conditions. For that reason, it is the standard of care for professional medical use. Patient inconvenience associated with the 12-lead Holter (see, e.g., FIG. 14) makes it impractical to wear more than 24 hours. Thus, it is appreciated that an ECG patch for multi week monitoring that combines the longer-term continuous monitoring capability with a 12-lead ECG capability would be of great value. Moreover, the patches may allow the monitoring of symptomatic episode while a subject is wearing a patch.

As described above, in general, the methods and apparatuses described herein may provide a set of substantially orthogonal cardiographic leads i.e. XYZ projections of heart vector and thus allow synthesis of a 12-lead recording, including in real or near-real time while patient is experiencing symptoms. A wearable patch ECG 12-lead ECG sensor as described herein may have a separation of about 5 cm and preferably 10 cm or more between sensing electrodes. To achieve a capability to record X, Y and Z projections of the heart vector with a patch, the patch may include the addition of two finger electrodes as well as a resistor network inside the ECG recording electronics of the patch. Any of these apparatuses may include resistive network as described above.

Figure 15:
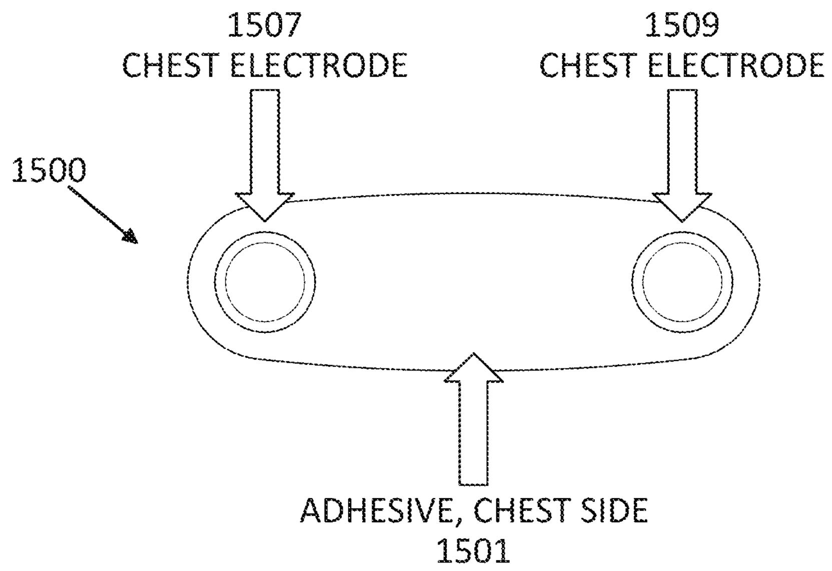
FIG. 15 shows a bottom view of one example of a view of an adhesive device (e.g., an XYZ patch) with adhesive chest electrodes.

For example, FIG. 15 illustrates one example of an ECG patch 1500 configured for 12-lead (or both 12-lead and 3 lead) detection as described herein, as an adhesive chest electrode. FIG. 15 shows a bottom view of the ECG patch 1500 for 12-lead detection. The pair of chest electrodes 1507, 1509 are arranged in line, separated by at least 10 cm, edge-to-edge. An adhesive 1501 may secure the device so that the electrodes are in electrical communication with the skin of the subject's chest. In some examples the adhesive is a medical adhesive that may secure the device to the chest for an extended period of time (e.g., days, weeks, etc.). In some examples the region over the electrodes does not include an adhesive. In some examples the region over the electrodes does include an adhesive, such as a conductive hydrogel.

Figure 13:
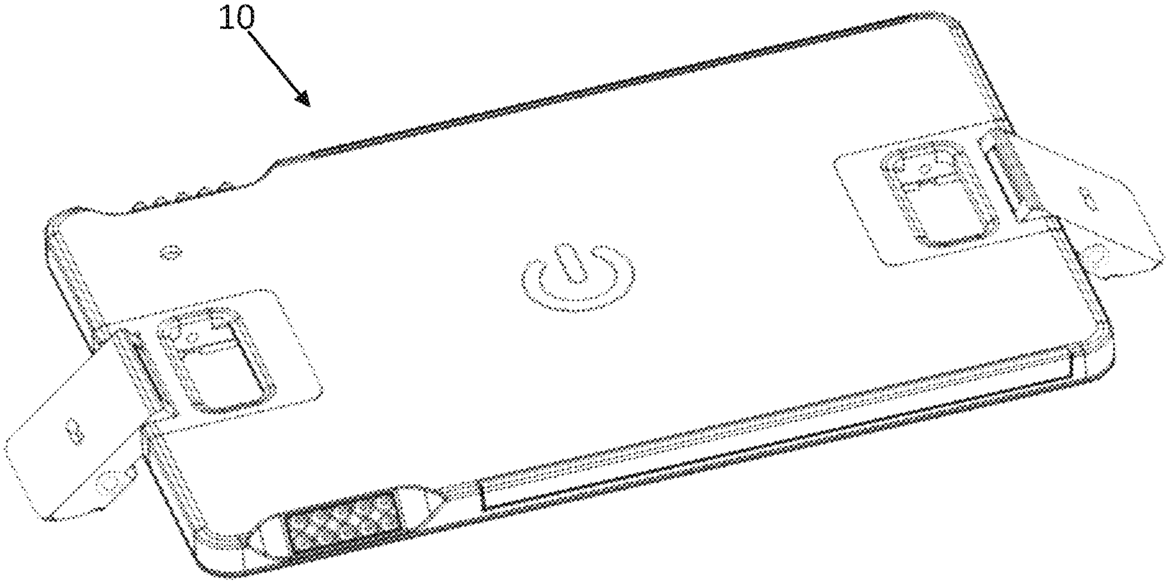
FIG. 13 shows one example of a hand-held ECG.
Figure 16:
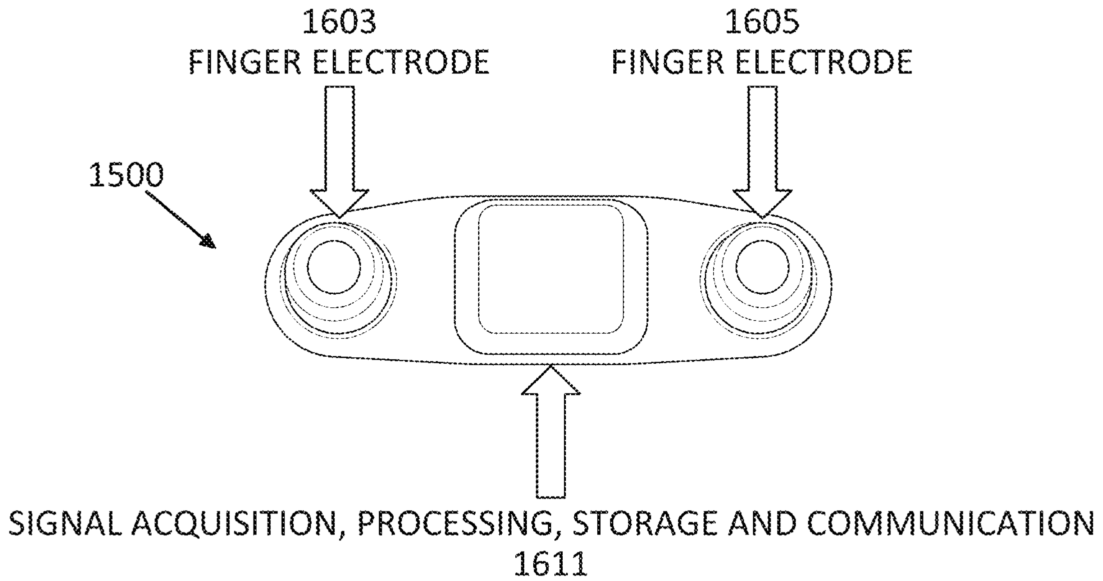
FIG. 16 shows a top view of the patch device of FIG. 15.

FIG. 16 shows a top view of the same device 1500, including two finger electrodes 1603, 1605. As shown, these finger electrodes are built into the top or side, e.g. non-adhesive surface, of the ECG patch for 12-lead detection. This configuration may ensure the functionality and diagnostic performance (similar or better than that described, for example, in the hand-held device shown in FIG. 13, and described in PCT/US2020/032556, incorporated by reference herein. In FIG. 16 the patch device also includes a body portion including one or more housings 1611 that may house any of the circuitry (e.g., the resistive network, wireless communication circuitry, etc.) discussed above. The device may not include a separate control, e.g., the control(s) may be the finger electrodes 1603, 1605 so that contacting the finger electrodes may trigger recording of signals from the electrode leads, including detection of a 12-lead ECG, processing locally (in the device), storing and/or transmitting to a remote site. In some examples the signals from the electrodes may be stored and/or transmitted for later analysis and/or review, including for later converting to a 12-lead signal. The system may also transmit the time of day. In some variations the system may also be configured to automatically or manually detect a one lead ECG signal (e.g., using just the two chest electrodes) or a 3 lead ECG signal. For example, the system may be configured to periodically detect electrical signals from the two (or more) chest electrodes 1507, 1509 when worn, and may store and/or transmit either the sensed electrical signals and/or a processed ECG signal. Alternatively or additionally the device my include a control or input (e.g., from a remote device, such as a smartphone or the like) for triggering measurement of a single-lead (or 3 lead) ECG detection. In some examples a single-lead (or 3 lead) measurement may be triggered when the user touches just one of the finger electrodes 1603, 1605. In some examples, the user (e.g., patient) may trigger measurement from all of the leads and/or processing to get a 12-lead ECG signal when the user touches multiple (e.g., both, three or more, etc.) finger electrodes for a sufficient time. During the period that the subject is touching the electrodes the system may record a signal. In some examples the device may detect contact, e.g., by a change in impedance from the electrodes. Alternatively or additionally, the device may include a control (button, switch, etc.) that may turn it "on" and/or move it from a standby to an active mode. In some examples one or both finger electrodes may also include a switch (e.g., a pressure-driven switch) that may turn the device on and/or move it from a standby to an active mode.

In some examples an ECG patch for 12-lead detection described herein may be referred to as "XYZ patch" devices. In general, these apparatuses (e.g., devices, systems, etc.) may include two finger electrodes on the top, non-adhesive side of the patch as shown in FIG. 16. The finger electrodes may be adapted for contact with the subject's right-hand finger and left-hand finger (right hand on the right side, left hand on the left side) and may be raised above the skin surface slightly, to prevent accidental contact with other parts of the body. The electrodes may be sized for contact with a sufficiently large region of the finger (e.g., between 5-15 mm diameter), and may be round, square, etc.

FIG. 16 also shows an enclosed compartment on the upper side of the patch that may also separate (and physically isolate) the left and right finger electrodes. In FIG. 16, the top view of the XYZ patch shows one or more housings or compartments 1611 that may house a power source (e.g., battery, etc.) and/or signal acquisition and processing electronic circuitry including the resistor network as well as signal storage and communication circuitry, as mentioned.

Figure 17:
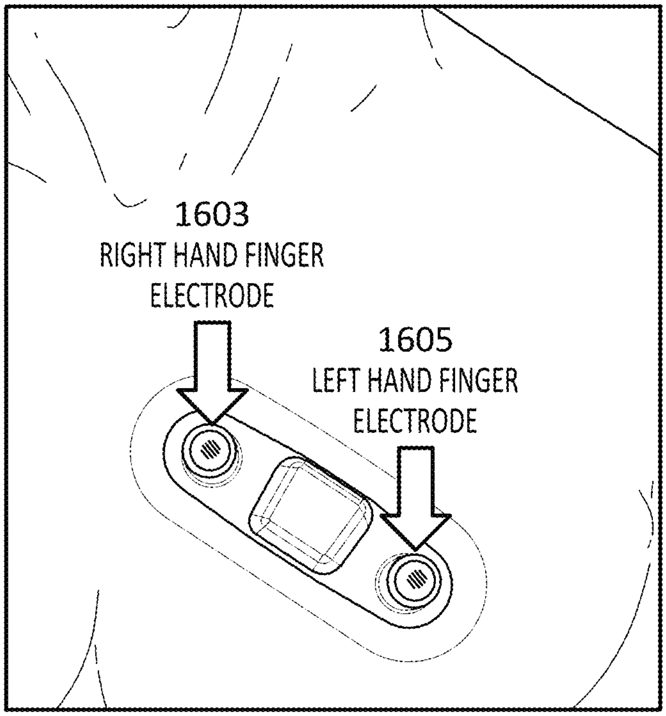
FIG. 17 shows one example of a patch device (e.g., an ECG patch for detecting 12 leads) attached to patient's chest.

FIG. 17 illustrates one example of an XYZ patch as worn by a patient. The patch is shown oriented with the right-hand electrode 1603 on the right side of the chest, slightly above the left-hand electrode 1605 that is on the left side of the chest. A measurement (which may include a symptomatic event) may be detected by placing fingers from the right and left hand on the corresponding finger electrodes. For example, in use the subject may place his fingers on both finger electrodes when he determines that an event may be occurring. Any finger pair of corresponding fingers from the left and right hand (e.g., index, pointer, pinky, thumb, etc.), that a subject prefers, is acceptable. In some examples a "symptoms present" button may be included on the device. Alternatively the electrode may be configured to detect a pattern of contact from the fingers that may indicate the subject is communicating symptoms are present. In some examples the patient (e.g., subject or user) may place his/her right-hand finger on the electrode that is at the higher elevation. The left-hand finger is placed on the other finger electrode on the lower elevation left hand, as shown in FIG. 18.

In some examples the apparatus may include a sensor or sensors to detect that the patch is oriented appropriately on the chest. For example, the patch may include a sensor to detect the orientation of the patch on the upright (or in some variations, prone) patient, such as an accelerometer. In addition, the device may be configured to detect skin contact with each of the electrodes, including the finger electrodes.

In operation of some examples, once skin contact is detected on both finger electrodes, the device will start recording X, Y and Z projections of the heart vector and by that enable synthesis of a 12-lead ECG signal that may correspond to a symptomatic event period. The recording may stop, and in some cases the system will continue in the single lead mode, as soon as at least one finger is removed from a finger electrode. Thus, recording may stop if at least one finger is removed from a finger electrode for at least a few seconds to avoid prematurely terminating a symptomatic session by accidental and short removal of a finger from a finger electrode. In some examples, for a period of time when only a single finger is contacting the device, a 3-lead ECG measurement may be taken and may automatically stop after a predetermined time period. In some examples, after both fingers are removed, additional single-lead measurements may be taken (e.g., single lead ECG) for a period of time, as this information may still have diagnostic value.

Figure 18:
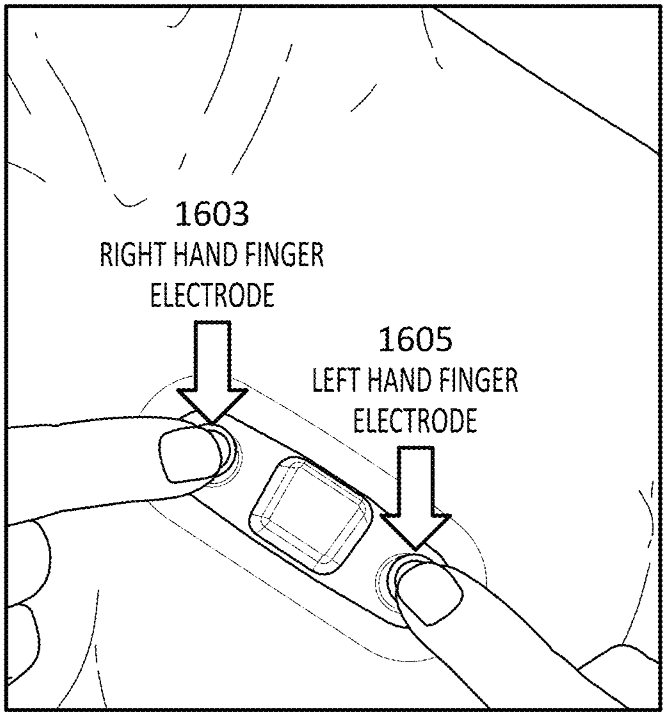
FIG. 18 illustrates one example of use of patient's fingers in an adhesive patch device.

FIG. 18 shows a symptomatic session recording with two fingers touching the finger electrodes on the top surface of an XYZ patch. Although the patch is shown in a specific location and angle in FIGS. 5-8, it could be placed in any position on the torso in the vicinity of the heart preferably with one finger electrode is visibly at a higher elevation than the other finger electrode.

In order to carry maximum diagnostic information, the XYZ leads may be as close to orthogonal as possible (e.g., three vector axes with 90 degrees angle between each of them). The opposite to orthogonal is the case of three coplanar vectors, that is three vectors in the same plane, in which case the diagnostic information corresponding to the axis perpendicular to that plane is completely missing.

The four recording electrodes configuration described above having two chest and two finger electrodes fulfill the requirement of high orthogonality. As described above, a simple way to fulfill this requirement is to record signals in three main body directions: lateral (left arm-right arm), sagittal (back-front) and caudal (head-toes). For example, the signal in the lateral direction is obtained by measuring the lead between left and right hand, the signal in the caudal direction is obtained by measuring the lead between the two chest electrodes, with the condition that the vertical distance between the chest electrodes is at least 5 cm (and preferably greater than about 10 cm), in order to be greater than the approximate diameter of the heart muscle. In an ideal case, the signal in the sagittal direction would be measured between the back and the chest of the patient, which is not possible with the constraint of using only finger and chest electrodes. To overcome this, a simple resistive network is used to make a reference point that is close to the heart electrical center, as described below. See also U.S. Pat. No. 10,117,592 B2, herein incorporated by reference in its entirety.

Figure 19:
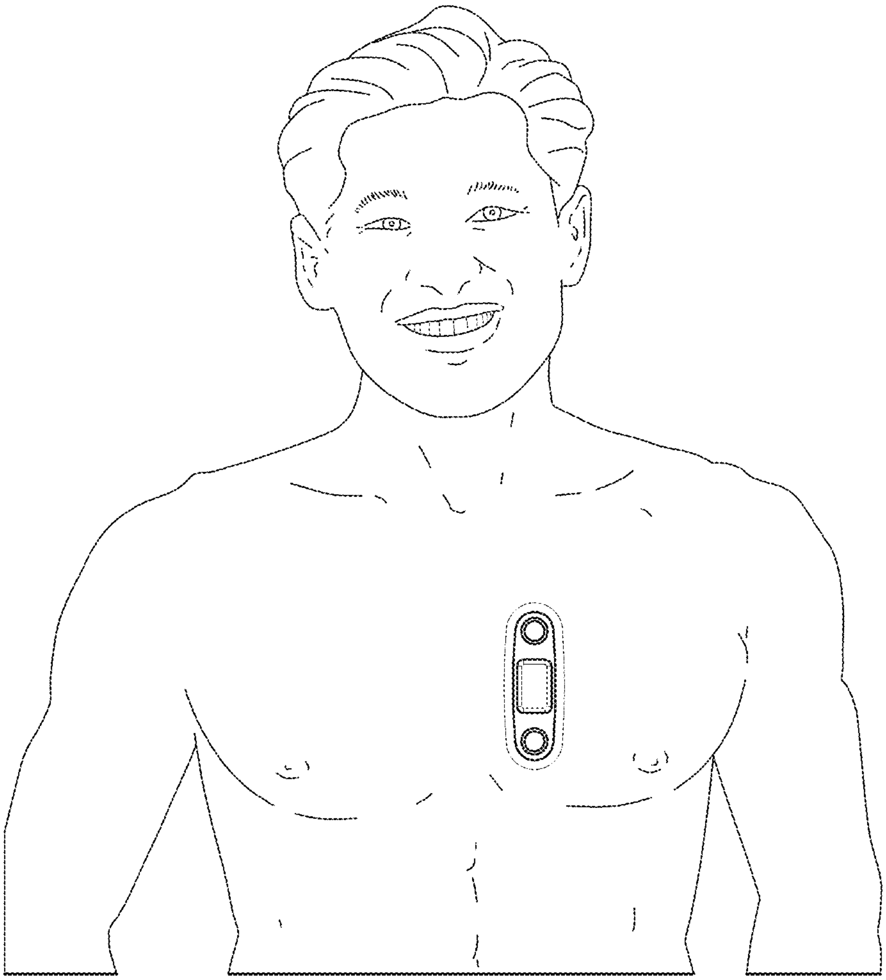
FIG. 19 illustrates one example of a vertically attached adhesive patch device.

The above description may explain why for the maximum orthogonality of recorded signals preferred attached position of the patch is that electrodes are approximately straight above each other (vertical position of the patch). This can be ensured by the use of a built-in accelerometer, as mentioned. This position of the patch on patient's torso is illustrated in FIG. 19. While compactness of the XYZ patch dictates that the finger electrodes be placed on the top or side surface of the patch, in some examples the finger electrodes can be engineered to be part of a separate pair of electrodes attached to the chest and to the patch. Alternatively, as will be described below in FIGS. 21A-21C, additional adhesive electrodes may be place on the limbs (as limb electrodes, e.g., on or near the shoulders) and may be used without the requirement for finger electrodes.

Any method of attaching finger electrodes to the patch may be used as long as two fingers are used in addition to two chest patch electrodes. The XYZ patches described herein may enable real-time or nearly real-time analysis of symptomatic evens. Unlike prior art devices in which an entire set of multi-week recordings are sent for analysis after the device is removed from the patient's chest, the apparatuses described herein may be operated in more real-time. These apparatuses may allow for the shortest time for analysis and possible diagnosis and intervention when reviewing a potentially symptomatic event. In some examples descriptions and corresponding ECG waveforms may be wirelessly sent in real time or nearly real time for a professional medical evaluation. As used herein, real time may include near real time (e.g., within a few minutes).

Figure 20A:
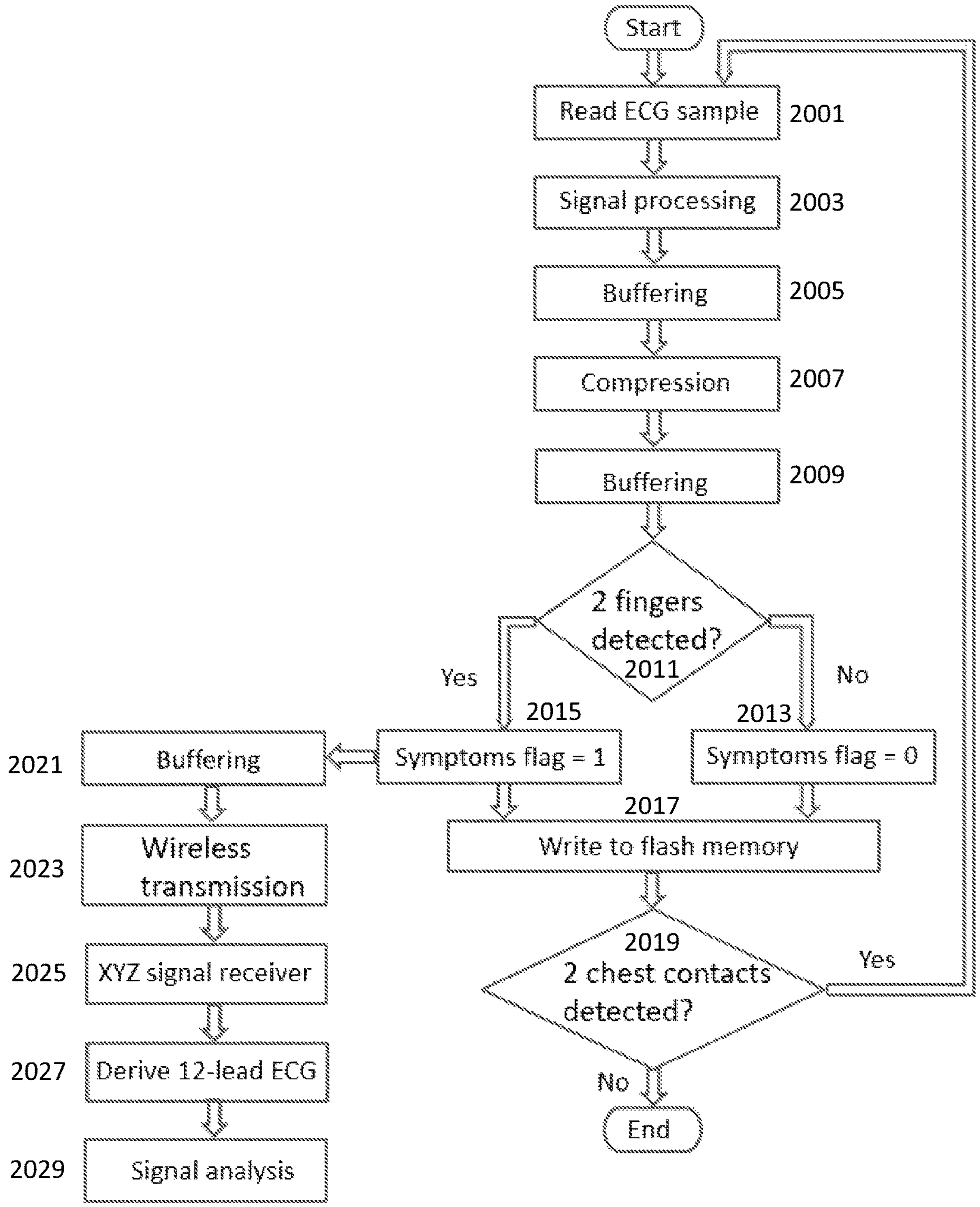
FIG. 20A schematically illustrates an example of a flow chart for an adhesive patch device as described herein.

FIG. 20A schematically illustrates one illustration of a system, shown as a system flow chart for an example of an XYZ patch. In FIG. 20A, ECG signal sampling 2001, processing 2003 buffering 2005 and/or compression 2007 may be done in any standard way from the signal(s) detected by the various electrode pairs (chest/chest, chest/left-finger, chest/right-finger, center point/left-finger, center point right-finger, etc.). For example, the sample signals may be stored and/or processed on the on-board circuitry (e.g., memory). In some examples, before a sample is written into the onboard flash memory it may be classified as part of a symptomatic episode or part of a routine non symptomatic single lead ECG recording section. The determination if a sample is part of a symptomatic episode could be made based on whether the patient pressed a "symptoms present" dedicated button or simply by detecting skin contacts on both finger electrodes (as shown in FIG. 18). In the latter case, patients may be instructed to touch finger electrodes and keep fingers on the finger electrodes while symptoms are present (e.g., by a signal, such as a tone or other sound, one or more LEDs, etc.). While the patient's fingers are touching finger electrodes the system may record 3 channels: X, Y and Z components of the heart vector. Alternatively or additionally, in some examples the apparatus can detect a dangerous heart rhythm (e.g., using just the two or more chest electrodes, such as 1-lead electrodes) while periodically or continuously monitoring the patient. If dangerous or irregular cardiac signal (e.g., irregular rhythms, AMI, tachycardia, etc.) are detected the apparatus may alert the user (via tone, text/SMS, vibration, etc.) to place their figures on the electrodes (indicating "symptoms present" 2011), as described in greater detail below. Thus, in general any of these apparatuses and methods may include ongoing, either periodic or continuous monitoring by the system.

In some examples, digital samples may be written into the onboard flash memory. Once the flash memory is removed from the patch it could be physically or electronically shared with a facility where the totality of the recording can be analyzed. Of special interest are signal sections of signals that may be associated symptomatic episodes. These episodes may feature XYZ signals and are converted from XYZ signals to 12-lead ECG signals and then analyzed.

All or some ECG signal samples may be streamed in real time to a communication device, such as a smartphone, that in turn communicates with the server, or with the help of a built-in communication module that communicates directly with a cloud-based server. This system is capable of transferring the totality of recorded signals in real time. As emphasized above, of particular interest are symptomatic episodes for the recording performed with a patch.

For example, returning to FIG. 20A, the methods described herein may detect that fingers are present on the electrodes 2011, as discussed above 2011, and may indicate (e.g., may flag 2015) that the signal is being recorded and flagged as potentially including an episode of cardiac difficulty or not 2013. As mentioned, the signal(s) may be annotated (e.g., with date, time, skin impedance data, etc.) and stored in device memory storage (such as a flash memory 2017) and/or processed 2019 as discussed above.

In some examples, in order to conserve power and/or time, the system may store all samples associated with a symptomatic episode in a dedicated memory sector or be able to extract it from the memory based on the particular symptomatic episode's unique flag. These samples may be buffered 2021, and/or transmitted 2023 via the onboard (to the patch) communication hardware and software in real time. For example, a Bluetooth connection from the patch to a patient's smart phone can be used for symptomatic session signal transmission and phone's Internet connectivity for the transfer on to the cloud. Initial automated diagnostic signal analysis can be performed in the cloud and from the cloud transferred to an analysis facility for a timely analysis by professional medical staff.

The methods and apparatuses (e.g., systems) described herein may sample the ECG (and in some examples perform an analysis) and transfer the samples (and/or the analysis) in real time for review by physicians, rather than downloading all signal samples after a delay (e.g., two weeks or more) and then sending them for analysis. This real time symptomatic episodes analysis is an improvement over current practice.

For every symptomatic session, a patient may be asked to report associated symptoms. This could be accomplished by voice recording and/or a form with standard questions or even a free format form written report by the patient on their smart phones.

FIG. 20A also describes real time analysis of symptomatic episodes. Recorded XYZ signals 2025 in a symptomatic session may be marked as symptomatic by setting the symptoms flag (e.g., to 1). In the next step they may be sent to the cloud where they are converted to a derived 12-lead ECG 2027. Typically, an automated diagnostic analysis 2029 that is performed in cloud follows. Alternatively or additionally, both derivation of the 12-lead and diagnostic analysis may be performed by the software that resides on the patient's smart phone. An integral part of signal analysis may review the recorded ECG signals by trained medical professionals after computerized analysis is done.

Figure 20B:
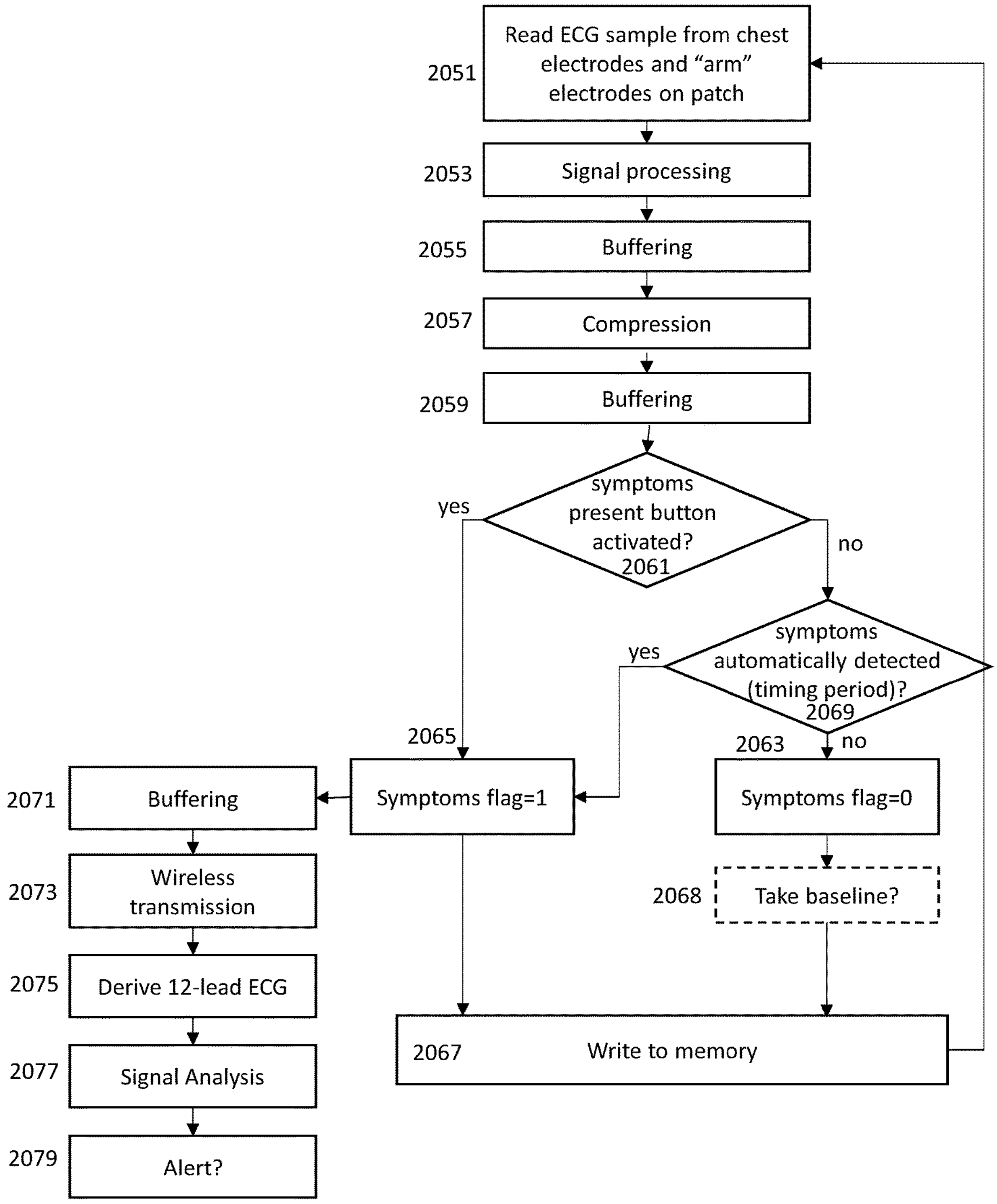
FIG. 20B schematically illustrates an example of a flow chart for an adhesive patch device including arm contacts as described herein.

FIG. 20B illustrates another example of a method of operating an apparatus as described herein, and in particular, a method of operating an adhesively-attached apparatus that includes one or more arm electrodes, as described in FIGS. 21A-21C, described in greater detail below. In these examples the apparatus may not need finger contact to derive 12-lead ECG signals.

Figure 12:
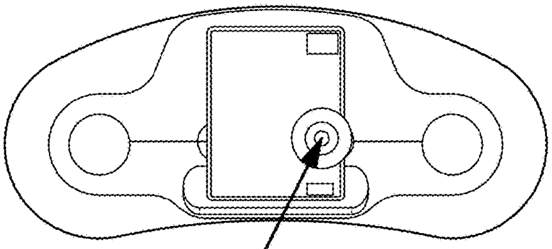
FIG. 12 (PRIOR ART)
FIG. 12 shows a prior art patch.

For example, in FIG. 20B, the apparatus may be configured to periodically or continuously monitor electrical signals from the two or more chest electrodes and the one or more arm electrodes on the adhesive patch (such as the adhesive patches shown in FIGS. 12A-12C). In one variation the system may monitor for activation of a user-activated "symptoms present" button and may then detect ECG signals that may be constructed into 12-lead ECG signals. In FIG. 20B, as described for FIG. 20A, ECG signal sampling 2051, processing 2053 buffering 2055 and/or compression 2057 may be done in any standard way from the signal(s) detected by the various electrode pairs (chest/chest, chest/left-arm, chest/right-arm, center point/left-arm, center point right-arm, etc.). For example, the sample signals may be stored and/or processed on the on-board circuitry (e.g., memory). In some examples, before a sample is written into the onboard flash memory it may be classified as part of a symptomatic episode or part of a routine non symptomatic single lead ECG recording section. The determination if a sample is part of a symptomatic episode could be made based on whether the patient pressed a "symptoms present" dedicated button.

The patient/user may activate the symptoms detected control ("symptoms detected button") when she or he experiences symptoms of a cardiac event 2061. As mentioned above, the apparatus may continuously or periodically (e.g., every few seconds, every 10 seconds, every 15 seconds, every 30 seconds, every minute, every 2 minutes, every 5 minutes, every 7 minutes, every 8 minutes, every 9 minutes, every 10 minutes, every 15 minutes, every 30 minutes, etc.) monitor the patient wearing the device and may detect an irregular cardiac signal (e.g., AMI, tachycardia, etc.). In some cases if the apparatus automatically detects an irregular cardiac signal the patient may be instructed to touch the symptoms present indicator (button, control, dial, etc.) when symptoms are present. Alternatively, when a patch with front finger electrodes is used, the detection of irregular cardiac signals may prompt the patient to touch with their fingers onto the finger electrodes (as shown in FIG. 18). Alternatively or additionally, in some examples the apparatus can detect a dangerous heart rhythm while periodically or continuously monitoring the patient. If dangerous rhythms (e.g., irregular rhythms, AMI, tachycardia, etc.) are detected the apparatus may flag the particular detected signal as potentially showing symptoms (e.g., by tripping the symptoms flag 2065) and/or alerting a caregiver and/or the user (via tone, text/SMS, vibration, etc.). Particularly, a patch such as that shown in FIG. 21C, may be employed for continuous monitoring of patient's cardiac activity with a goal to detect AMI. The orthogonal lead system described above can be readily acquired by the patch FIG. 21C on a periodic or continuous basis. Algorithms described herein can then be employed to detect occurrence of AMI events and trigger appropriate alerts. Thus, in general any of these apparatuses and methods may include ongoing, either periodic or continuous monitoring by the system.

If the system does not either detect an irregular cardiac signal and/or the user is not actuating the symptoms present button, the apparatus may set the symptoms flag to null 2063, and in some cases may take a baseline signal 2068. The baseline may be used by the system in a patient-specific manner to refine the detection of irregular cardiac signals and/or the 12-lead ECG. Baseline signals may be determined at some frequency (e.g., every minute, every few minutes, every 2 minutes, every 5 minutes, every 10 minutes, every 15 minutes, every 20 minutes, every 30 minutes, every 45 minutes, every hour, every 2 hours, every 4 hours, every 8 hours, every 12 hours, every day, every 2 days, every 5 days, every 7 days, etc.).

As mentioned, digital samples may be written into the onboard flash memory 2067 and/or transmitted 2073 (e.g., after signal processing, such as buffering 2071, etc.). Once the flash memory is removed from the patch it could be physically or electronically shared with a facility where the totality of the recording can be analyzed. Of special interest are signal sections of signals that may be associated symptomatic episodes. The signals may be used to generate 12 lead ECG signals from the subset of leads recorded 2075. Signal analysis may be used to interpret the 12-lead ECG signals 2077, including detecting a cardiac episode. These episodes may feature XYZ signals and are converted from XYZ signals to 12-lead ECG signals and then analyzed.

All or some ECG signal samples may be streamed in real time or near-real time (or after storage) 2073 to a communication device, such as a smartphone, that in turn communicates with the server, or with the help of a built-in communication module that communicates directly with a cloud-based server. This system is capable of transferring the totality of recorded signals in real time. As emphasized above, of particular interest are symptomatic episodes for the recording performed with a patch.

For example, in FIG. 20B, the methods described herein may detect and record a signal and may flag one or more signals as potentially including an episode of cardiac difficulty 2063 (or may flag it as not indicating cardiac difficulty). As mentioned, the signal(s) may be annotated (e.g., with date, time, skin impedance data, etc.) for transmission and/or stored in device memory storage (such as a flash memory 2067) and/or processed 2069 as discussed above.

In some examples, in order to conserve power and/or time, the system may store all samples associated with a symptomatic episode in a dedicated memory sector or be able to extract it from the memory based on the particular symptomatic episode's unique flag. These samples may be buffered 2061, and/or transmitted 2063 via the onboard (to the patch) communication hardware and software in real time. For example, a Bluetooth connection from the patch to a patient's smart phone can be used for symptomatic session signal transmission and phone's Internet connectivity for the transfer on to the cloud. Initial automated diagnostic signal analysis can be performed in the cloud and from the cloud transferred to an analysis facility for a timely analysis by professional medical staff.

Once the patient finishes wearing the patch that the totality of a multi-day recording can be analyzed in many different ways. While the real time transmission and analysis of signals associated with symptomatic episodes is highly desirable, it is not mandatory, and it could be postponed to the time when the patch is removed from the patient's body.

As mentioned, the patch apparatuses described herein may use a simple resistive network to make a central point (CP) that is close to the heart electrical center. For recording a lead in approximately sagittal direction, we record the voltage of the lower chest electrode with respect to a central point (CP), obtained using two hand electrodes and two resistors. The two resistors may be equal, approximately 5 kOhm (kΩ) each, or unequal, the first one approximately 5 kOhm (kΩ) between the left-hand electrode and the CP, and the second one approximately 10 kOhm (kΩ) between the right-hand electrode and the CP. This asymmetry reflects the left-side position of the heart in the torso, thus shifting the CP at the approximate electrical center of the heart. In this way, we obtain a three-lead system that are substantially orthogonal. Other lead configurations with or without CP may also be used.

The XYZ patch may incorporate cardiac signal recording circuitry including amplifiers and AD convertor for amplifying the signals detected by the electrodes, data storage circuitry (e.g., memory) for storing the recording signal, communication circuitry operating on GSM, WWAN, or a similar telecommunication standard for communication with the remote processor (e.g., PC computer, pad, smartphone, etc.) and circuitry (e.g. screen, speaker, etc.) for communicating diagnostic information to the user in the form of visual and/or audio output.

The hand-held device with special electrode configurations is capable of recording three orthogonal cardiac lead signals in an orientation-specific manner, and transmitting these signals to a processor (e.g., PC or other computing device). The remote processor may be configured to diagnose/detect AMI and transmit the diagnostic information back to the hand-held device.

A remote processor may be equipped with diagnostic software for processing the received cardiac signals, producing diagnostic information and for transmitting the information back to the hand-held device for communicating the diagnostic information to the patient. The device may be capable of performing automated detection of a cardiac condition on the basis of a 3-lead system and may not require interpretation of the processed diagnostic information by a specialist.

The signal processing and diagnostic software can also be run on the processor (e.g., microprocessor) integrated in the casing of the hand-held device for processing the recorded cardiac signals and producing diagnostic information. When the diagnostic processing is carried out by a remote processor, a backup version of the software running on the microprocessor may be integrated in the hand-held device and may be used in situations when the user is in a zone without wireless network coverage.

The device may be communicating with the remote processor via integrated communication circuitry. The remote processor may communicate with the hand-held device via integrated communication module. The created diagnostic information may be transmitted from the remote processor (e.g., a PC computer, server, etc.) to the device memory via commercial communication network. The hand-held device may communicate the diagnostic information to the patient via characteristic sounds via acoustic sensor producing characteristic sounds, voice massages or in the form of graphical information via a display integrated in the device.

In general, the analysis may include the analysis of a baseline. A baseline ECG (e.g., a baseline heart vector) may be taken at the time the patient first subscribes and/or purchases the apparatus. The baseline signal may be vetted by the system. For example, the baseline signal may be examined to confirm that it is within some predefined 'normal' range of parameters. For example, the patent's baseline signal may be determined by doing a differential vector analysis of the baseline heart vector determined from the three orthogonal leads of the signal collection device. Multiple baseline measurements may be made and averaged, or the best one may be selected. Patients may be rejected as poor candidates where the baseline does not fall within expected parameters, e.g., because they have an irregular heart vector for some reason (including concurrent, undetected cardiac event). The system may periodically prompt the user to provide updated baseline signals.

In some variations the application software may provide quality control (QC) to check signals (e.g., a QC agent, a software agent, etc.), which may indicate that the baseline heart vector is sufficient or not; this may be done in real time, and may include both a signal quality check, which may be done at either or both the signal collection device and the mobile communications device (e.g., smartphone) and/or at the remote server. The QC agent may look for clarity of signal and/or may also confirm that the patient is not having heart attack. This may be part of a final level quality check.

The application software/firmware may also acquire risk factors from the patient. This may advantageously be done at the time of subscription. The patient may be prompted with a series of questions and/or may provide access to electronic medical records, indicating risk factors that are associated with a heart disorder (e.g., heart attack, etc.). Information may include patient-specific information (age, gender, weight, height, ethnicity, cholesterol level(s), blood pressure, etc.). The inquiry may be ordered and weighted. A minimum entry of risk factor information may be permitted (e.g., just age, just age and gender, etc.); if the minimum is not entered, the patient may not be permitted to subscribe.

As mentioned, the application may prompt the patient to update the baseline periodically (e.g., weekly, bimonthly, monthly, etc.) by sending messages (SMS/text messages) in an associated application software (app) or without the app (from the remote server).

In some variations a report may be made to a physician that may then interpret the results manually or semi-manually, including the risk factors and symptoms, and may contact the patient directly, including through the app.

For example, a mobile three-lead cardiac monitoring device having a first compact and undeployed configuration and a second deployed configuration as described herein may be configured to be operated by a patient when cardiac symptoms occur. The device may include a storage (e.g., memory) for storing data on patient's cardiac risk factors and other data, cardiac signals recording components (e.g., electrodes, circuitry, controller) for recording a patient's cardiac signals; the recording components may be similar to those disclosed in WO2016/164888A1, Bojovic et al, mentioned above. Patient related data (risk factors and current symptoms) may be entered, and diagnostic message may be communicated to the patient, by equipping the device with a graphical user interface (e.g., touch screen or screen and a keyboard, etc.). The diagnostic information can also or alternatively be communicated to the patient via speaker through characteristic sounds or voice messages. The communication may occur via wired or wireless connection to a separate user-operated device, such as a smartphone or tablet, etc.

As mentioned, in some examples the four recording electrode configuration (e.g., having two chest and two finger electrodes) may fulfill the condition of high orthogonality, e.g., by recording signals in three main body directions: lateral (left arm-right arm), sagittal (back-front) and caudal (head-toes). For example, the signal in the lateral direction may be obtained by measuring the lead between left and right hand. The signal in the caudal direction may be obtained by measuring the lead between the two chest electrodes, with the condition that the distance between the chest electrodes in caudal direction is at least 5 cm, preferably greater than about 10 cm, in order to be greater than the approximate diameter of the heart muscle. In an ideal case, the signal in the sagittal direction would be measured between the back and the chest of the patient, using a simple resistive network to make a central point (CP) that is close to the heart electrical center. For recording a lead in approximately sagittal direction, we record the voltage of the lower chest electrode with respect to a central point (CP), obtained using two hand electrodes and two resistors. The two resistors may be equal, approximately 5 kOHM each, or unequal, the first one approximately 5 kOHM between the left-hand electrode and the CP, and the second one approximately 10 kOHM between the right-hand electrode and the CP. This asymmetry reflects the left-side position of the heart in the torso, thus shifting the CP at the approximate electrical center of the heart. In this way, we obtain a three-lead system that are substantially orthogonal.

Other similar lead configurations with the same CP may be chosen using the same set of two chest and two hand electrodes. Such a lead configuration may be substantially orthogonal, for example when both chest electrodes are used to record leads with the reference pole at the CP. Another possibility to define CP is using three electrodes, two hand electrodes and one chest electrode, and 3 resistors connected in a Y (star) configuration.

Other lead configurations without CP may also be used, like the configuration recording the signal of two chest electrodes and right-hand electrode with respect to left hand electrode. Such configurations without resistors or CP are more noise resistant to, for example, 50-60 Hz electrical noise, but have less orthogonal lead directions than the described ones using a CP. Generally, any other lead configuration using the same four described electrodes (a total of 20 configurations without a CP) results in leads that are non-coplanar and as such capture diagnostic signal in all three directions but may lack a high degree of orthogonality. However, these configurations may have different levels of orthogonality, depending on the use of the right-hand electrode. The configuration using the right-hand electrode as the common reference pole in all 3 leads may have the lowest orthogonality, since the right-hand electrode is farthest from the heart among the four electrodes, and thus the angles between the vectors corresponding to the three leads are the smallest. However, this configuration with the lowest orthogonality is optimal for reconstruction of 12 leads ECG based on 3 lead signal, due to its small non-dipolar content. Nevertheless, the signals obtained using this configuration may be used with or without 12 leads reconstruction.

The effectiveness of the described solution is not affected if one or more chest electrodes are added on the back side of the device, and one or more corresponding additional leads are recorded and used in diagnostic algorithms. Also, the effectiveness will not be affected if front electrodes are pressed with palms or any other part of hands instead with the fingers.

For example, the apparatuses described herein may be used for remote diagnostics of cardiac conditions, such as acute myocardial infarction (AMI), atrial fibrillation (AFib), or the like. In particular, described herein are handheld devices with special electrode configurations capable of recording three orthogonal cardiac lead signals in an orientation-specific manner, and transmitting these signals to a processor (e.g., PC or other computing device). The processor may be configured to diagnose/detect AMI and transmit the diagnostic information back to the handheld device. The handheld device may communicate the diagnostic information to the patient via characteristic sounds, voice messages or via a graphical display. The processor may be configured via hardware, software, firmware, or the like, and may process the signals received to produce a difference signal and extract information reliably related to detection of AMI (and additional information of clinical relevance). Thus, these apparatuses and methods may perform automated detection of cardiac conditions on the basis of a 3-lead system, without the necessity for 12L ECG reconstruction, reducing or eliminating the need for medical personnel to interpret the ECG, unlike prior art systems, which typically rely on medical personnel for such decisions. The automated diagnostic methods described herein, in combination with the improved handheld cardiac devices, address many of the needs and problems present in other systems.

The patch devices described herein may be positioned on the chest with the center of the device on the left side of the chest approximately above the center of the heart muscle. In this position, the chest electrodes are approximately on the midclavicular line, the vertical line passing through the midpoint of the clavicle bone, same as for the V4 electrode of the conventional ECG, and the lower chest electrode is at about the level of the lower end of the sternum. A signal in the lateral direction may be obtained by measuring the lead between left and right hand. The signal in the caudal direction may be obtained by measuring the lead between the two chest electrodes, with the condition that the distance between the chest electrodes in caudal direction is at least 5 cm, preferably greater than about 10 cm, in order to be greater than the approximate diameter of the heart muscle.

As already described above, the example in FIG. 3A shows a simple electrical scheme for obtaining a central point CP by connecting the electrodes of both hands via a simple resistive network with two resistors. Alternatively, the op-amp scheme in FIG. 3B can be used. The same configuration shown and described above in FIGS. 3, 4A-4G may be used with any of the adhesive devices described herein. For example, for recording a lead in approximately sagittal direction, the voltage of the lower chest electrode B with respect to a central point CP may be obtained using the hand electrodes C, D and two resistors R1, R2. The two resistors R1, R2 can be equal, approximately 5 kΩ each, or unequal, approximately 5 kΩ between the left-hand electrode and the CP, and 10 kΩ between the right-hand electrode and the CP. This asymmetry may reflect the left-side position of the heart in the torso, thus putting the CP point at the approximate electrical center of the heart. In this way a substantially orthogonal three lead configuration may be obtained.

Examples

Figure 21A:
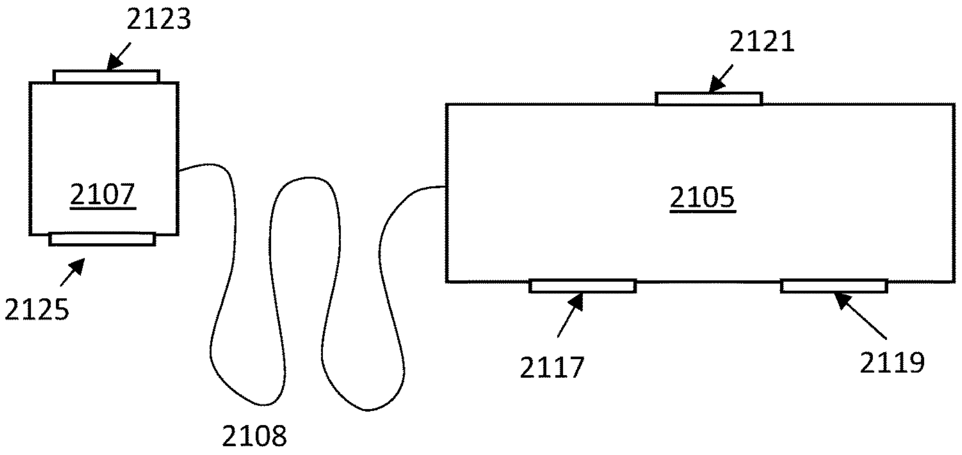
FIGS. 21A-21C illustrate alternative examples of adhesive patch devices as described herein.

FIG. 21A illustrates another example of a patch (e.g., adhesive) apparatus for long-term monitoring and detection of 12-lead equivalent ECGs. In FIG. 21, rather than all of the finger electrodes being coupled to the same housing, the patient (or a caregiver or medical professional) may separately attach the housing having at least two skin-contacting ("chest") electrodes 2105 that may be coupled by a wire 2108 connecting the chest electrodes 2117, 2119 (and one or more finger electrodes 2121) to a separate patch 2107 that includes a second finger electrode and/or an arm electrode 2125. In some examples the separate patch may be adhesively secured to the shoulder or arm (e.g., left shoulder/arm) and used instead of the derived arm lead. The second finger electrode 2123 in this example may be omitted or may be used as a reference.

Figure 21B:
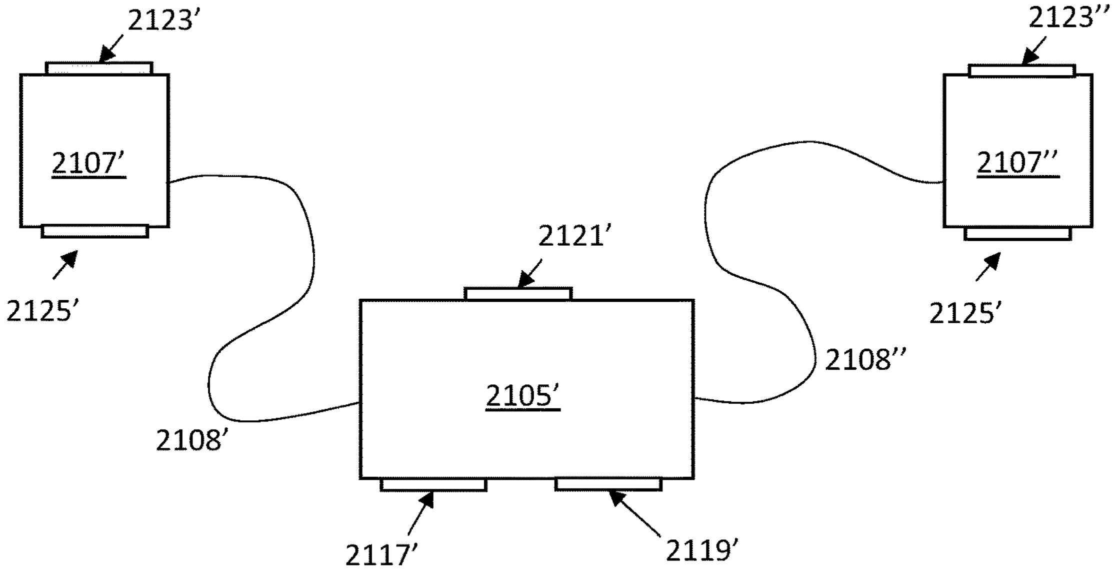

FIG. 21B shows another example of a patch device with a center, heart, patch region 2105' that is electrically coupled via a pair of tethers 2108, 2108' to a pair of separate finger or arm patches 2107', 2107". In this example, each arm patch may be attached to the subject's shoulders or arms for measuring leads from each arm, rather than deriving this from finger electrodes. Optional finger electrodes 2123', 2123" may also be included. In FIGS. 21A-21B the thicknesses of the patches are not shown to scale but are shown schematically exaggerated. The patches may be made of a flexible and relatively thin material.

In some variations it may be beneficial to include a single piece that adhesively attaches to the skin, rather than two or more separate adhesive patches. For example, FIG. 21C illustrates an example of a patch device that may include extensions (arms, wings, etc.) for adhesively securing arm electrodes on the right and left arm (e.g., shoulder) regions. In FIG. 21C the bottom of the device is shown, showing the electrodes, including the chest electrodes 2117", 2119", left arm electrode 2123'" and right arm electrode 2123"". The housing portion 2135 of the device may be offset relative to the two arm electrodes (e.g., so as to be positioned over the heart region of the chest when worn). In some examples the device may also include one or more controls, e.g., buttons, that may be on the non-adhesive side (not shown) that may allow the device to be triggered to record or to associate a recording as an event. The examples shown in FIGS. 21A-21C may allow for continuous or periodic 12-lead ECG detection without requiring the user to touch finger electrodes. Thus, baseline 12-lead ECG measurements may be taken and used to normalize or adjust the measurements to increase accuracy. The device shown in FIG. 21C may be provided in a variety of predetermined sizes (e.g., small, medium, large) and/or may adjustable.

Figure 21C:
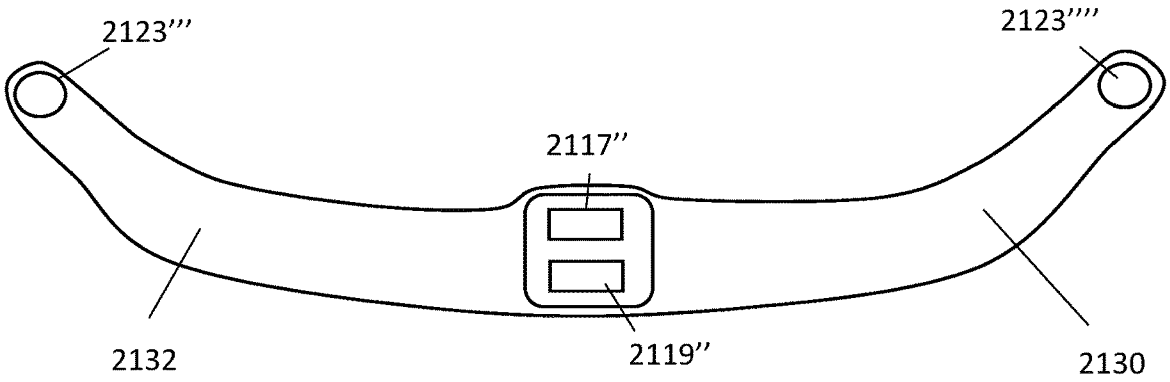

The example shown in FIG. 21C is a continuous patch in which the arm extensions 2130, 2132 extend from a central chest region that is applied as described above. As mentioned, in some examples the left arm extension 2130 may be shorter or longer than the right arm extension 2132 or they may be the same size. For example, in some cases the left arm extension (to be worn on the left side of the patient's chest) is shorter, so that the chest electrodes may be positioned more closely over the heart. The chest arm extensions may be between, e.g., 2 inches and 12 inches long; the total length (from left arm electrode to right arm electrode) may be between 6 and 16 inches (e.g., between 8 and 16 inches, between 6 and 15 inches, between 7 and 14 inches, etc.).

As described above, an adhesive patch device such as the one shown in FIG. 21C may be operated as described in FIG. 20B, above.

A clinical study was done to evaluate the diagnostic accuracy of the methods described above for detecting myocardial ischemia provoked by balloon inflation in coronary arteries during a PCI (Percutaneous Coronary Intervention) procedure. A device similar to that shown in FIG. 2C was used.

In this example, data was acquired continuously. Continuous data from standard 12 lead ECG with additional three special leads were obtained from each patient during the entire period of balloon occlusion, and for a short period before and after. Target duration for balloon occlusion was at least 90 sec if the patient is stable. In each patient, one baseline recording was taken prior to the beginning of the PCI procedure, and one pre-inflation during the procedure, prior to first balloon insertion. In each lesion/intervention site, one inflation recording was taken just before the balloon deflation. The analyzed data set contains ECG recordings of 66 patients and 120 balloon occlusions (up to three arteries inflated per patient).

Data was analyzed by the methods described above (using the embodiment with a linear combination of STVM and "Clew" markers), and results were compared to the interpretation of the same data set by three experienced cardiologists (one interventional cardiologist, two cardiac electrophysiologists), blinded to any clinical data. All inflation recordings were assumed to be ischemia-positive and all pre-inflation recordings to be ischemia-negative. The study data set was divided into two sets of approximately same sizes, learning and test sets (using a random number generator). The markers for ischemia detection were chosen and marker thresholds tuned on the learning set before the algorithm was applied to the test set.

Table 1, below illustrates the results of this study, comparing automatically scored readings with readings scored by human (e.g., cardiologist), showing a greater success rate using the automatic methods described herein compared to those of trained human experts (human reader's average).

TABLE 1

Sensitivity, specificity and accuracy of the automated method compared to human expert reading.

| | SEN [%] | SPE [%] | ACC[%] |
|---|---|---|---|
| Automated method | 89.06 | 91.18 | 89.80 |
| Human readers | 76.11 | 64.14 | 71.86 |
| Difference | 12.95 | 27.04 | 17.93 |

The results given in Table 1 show the superiority of using the availability of the reference baseline cardiac recording for distinguishing new from old ST deviation.

Another clinical study was done to evaluate the diagnostic accuracy of the algorithm based on 3 orthogonal cardiac leads in detecting Atrial Fibrillation. The data set included 453 recordings from 25 patients after Pulmonary Vein Isolation (227 recordings with sinus rhythm and 226 with Atrial Fibrillation). The "Clew" marker was applied to the P wave, combined with commonly used RR interval marker. Table 1 below illustrates the results of this study.

TABLE 2

Performance of the automated method in detecting Atrial Fibrillation

| | SEN [%] | SPE [%] | ACC [%] |
|---|---|---|---|
| Automated method | 99.12 | 92.04 | 95.58 |

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word “comprise”, and variations such as “comprises” and “comprising” means various components can be co-jointly employed in the methods and articles (e.g., compositions and apparatuses including device and methods). For example, the term “comprising” will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive and may be expressed as “consisting of” or alternatively “consisting essentially of” the various components, steps, sub-components or sub-steps.

As used herein in the specification and claims, including as used in the examples and unless otherwise expressly specified, all numbers may be read as if prefaced by the word “about” or “approximately,” even if the term does not expressly appear. The phrase “about” or “approximately” may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value “10” is disclosed, then “about 10” is also disclosed. Any numerical range recited herein is intended to include all sub-ranges subsumed therein. It is also understood that when a value is disclosed that “less than or equal to” the value, “greater than or equal to the value” and possible ranges between values are also disclosed, as appropriately understood by the skilled artisan. For example, if the value “X” is disclosed the “less than or equal to X” as well as “greater than or equal to X” (e.g., where X is a numerical value) is also disclosed. It is also understood that the throughout the application, data is provided in a number of different formats, and that this data, represents endpoints and starting points, and ranges for any combination of the data points. For example, if a particular data point “10” and a particular data point “15” are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term “invention” merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An adhesive patch device for synthesizing a 12-lead electrocardiogram (ECG), the device comprising:

a patch of adhesive material having a back and a front, wherein the back is configured to be adhesively secured to a patient’s chest;

a first electrode and a second electrode integrated on the back of the patch configured to measure bioelectric signals from the patient’s chest, wherein the first and second electrodes are positioned a distance of at least 5 cm apart;

a third electrode on the front of the patch and configured to measure bioelectric signals from the patient’s right hand;

a fourth electrode on the front of the patch and configured to measure bioelectric signals from the patient’s left hand;

a processor, within a housing of the patch, configured to derive three orthogonal cardiac leads from the first, second, third and fourth electrodes; and a detection circuit configured to detect finger contact on both the third electrode and the fourth electrode, wherein the processor is configured to operate in a first mode, collect the three orthogonal cardiac leads, and indicate that the three orthogonal cardiac leads are associated with a cardiac event when the detection circuit detects the finger contact on both the third electrode and the fourth electrode, wherein the detection circuit is further configured to detect that both the third electrode and the fourth electrode are not contacting a finger and wherein the processor is further configured to automatically operate in a second mode, detect an irregular cardiac signal in a one-lead ECG signal from the first electrode and the second electrode when the detection circuit detects that both the third electrode and the fourth electrode are not contacting the finger, and prompt the patient to touch the third electrode and the fourth electrode when the irregular cardiac signal is detected in the one-lead ECG signal, and wherein the first electrode is disposed substantially over the third electrode and the second electrode is disposed substantially over the fourth electrode.

2. The device of claim 1, further comprising a communication circuit within the housing configured to transmit the processed three orthogonal cardiac leads to a remote processor.

3. The device of claim 1, further comprising a marker on the housing indicating an orientation of the patch when applied to the patient's chest.

4. The device of claim 1, further comprising an LED on the housing indicating an orientation of the housing.

5. The device of claim 1, wherein the third and fourth electrodes are disposed on two opposed sides with respect to a longitudinal plane of symmetry of the housing, said longitudinal plane of symmetry being substantially perpendicular to the back of the housing.

6. The device of claim 1, further comprising a ground electrode on the housing for contacting one of the patient's hands disposed on either a side or a front of the housing.

7. The device of claim 1, wherein either the third or fourth electrode is band-shaped and disposed along a first side of the housing.

8. The device of claim 1, further comprising a symptoms present input on the patch, wherein the processor is configured so that the three orthogonal cardiac leads derived from the first, second, third and fourth electrodes are marked by a flag indicating that the patient has activated the symptoms present input.

9. An adhesive patch device for synthesizing a 12-lead electrocardiogram (ECG), the device comprising:

a patch of adhesive material having a back and a front, wherein the back is configured to be adhesively secured to a patient's chest;

a first electrode and a second electrode integrated on the back of the patch configured to measure bioelectric signals from the patient's chest, wherein the first and second electrodes are positioned a distance of at least 5 cm apart;

a third electrode on the front of the patch and configured to measure bioelectric signals from the patient's right hand;

a fourth electrode on the front of the patch and configured to measure bioelectric signals from the patient's left hand, wherein the third and fourth electrodes are disposed on opposed sides with respect to a longitudinal plane of symmetry that is substantially perpendicular to the back of a housing, wherein the first electrode is disposed substantially over the third electrode and the second electrode is disposed substantially over the fourth electrode;

a processor, within the housing of the patch, configured to derive three orthogonal cardiac leads from the first, second, third and fourth electrodes; and a detection circuit configured to detect finger contact on both the third electrode and the fourth electrode, wherein the processor is configured to operate in a first mode, collect the three orthogonal cardiac leads, and indicate that the three orthogonal cardiac leads are associated with a cardiac event when the detection circuit detects the finger contact on both the third electrode and the fourth electrode, wherein the detection circuit is further configured to detect that the third electrode and the fourth electrode are not contacting a finger, wherein the processor is further configured to automatically operate in a second mode and detect a one-lead ECG signal from the first electrode and the second electrode when the detection circuit detects that both the third electrode and the fourth electrode are not contacting the finger, and wherein the processor is configured to detect an irregular cardiac signal from the one-lead ECG signal and to prompt the patient to touch the third electrode and the fourth electrode when the irregular cardiac signal is detected.

10. The device of claim 9, further comprising a communication circuit within the housing configured to transmit the processed three orthogonal cardiac leads to a remote processor.

11. The device of claim 9, further comprising a marker on the housing indicating an orientation of the patch when applied to the patient's chest.

12. The device of claim 9, further comprising an LED on the housing indicating an orientation of the housing.

13. The device of claim 9, further comprising a ground electrode on the housing for contacting one of the patient's hands disposed on either a side or a front of the housing.

14. The device of claim 9, wherein either the third or fourth electrode is band-shaped and disposed along a first side of the housing.

15. The device of claim 9, further comprising a symptoms present input on the patch, wherein the processor is configured so that the three orthogonal cardiac leads derived from the first, second, third and fourth electrodes are marked by a flag indicating that the patient has activated the symptoms present input.

16. An adhesive patch device for synthesizing a 12-lead electrocardiogram (ECG), the device comprising:

a patch of adhesive material having a back and a front, wherein the back is configured to be adhesively secured to a patient's chest;

a first electrode and a second electrode integrated on the back of the patch configured to measure bioelectric signals from the patient's chest;

a third electrode on the front of the patch and configured to measure bioelectric signals from the patient's right hand;

a fourth electrode on the front of the patch and configured to measure bioelectric signals from the patient's left hand, wherein the third and fourth electrodes are disposed on opposed sides with respect to a longitudinal plane of symmetry that is substantially perpendicular to the back of a housing, wherein the first electrode is disposed substantially over the third electrode and the second electrode is disposed substantially over the fourth electrode;

a processor, within the housing of the patch, configured to derive three orthogonal cardiac leads from the first, second, third and fourth electrodes; and a detection circuit configured to detect finger contact on both the third electrode and the fourth electrode, wherein the processor is configured to operate in a first mode, collect the three orthogonal cardiac leads, and indicate that the three orthogonal cardiac leads are associated with a cardiac event when the detection circuit detects the finger contact on both the third electrode and the fourth electrode, further wherein the detection circuit is further configured to detect no finger contact on both the third electrode and the fourth electrode and the processor is further configured to automatically operate in a second mode and detect an irregular cardiac signal in a one-lead ECG signal from the first electrode and the second electrode when the detection circuit detects no finger contact on both the third electrode and the fourth electrode, and prompt the patient to touch the third electrode and the fourth electrode when the irregular cardiac signal is detected in the one-lead ECG signal.

17. The adhesive patch of claim 16, wherein the detection circuit is further configured to detect that finger contact has been removed from both the third electrode and the fourth electrode and wherein the processor is further configured to detect the one-lead ECG signal from the first electrode and the second electrode when the detection circuit detects that finger contact has been removed from both the third electrode and the fourth electrode.

* * * * *